US012408920B2

(12) United States Patent
Gagner et al.

(10) Patent No.: US 12,408,920 B2
(45) Date of Patent: *Sep. 9, 2025

(54) ANASTOMOSIS FORMATION WITH MAGNETIC DEVICES HAVING BIORESORBABLE RETENTION MEMBER

(71) Applicant: GT METABOLIC SOLUTIONS, INC., Wilmington, DE (US)

(72) Inventors: Michel Gagner, Montréal (CA); Todd A. Krinke, Buffalo, MN (US); Thierry Thaure, San Jose, CA (US)

(73) Assignee: GT METABOLIC SOLUTIONS, INC., Wilmington, DE (US)

( * ) Notice: Subject to any disclaimer, the term of this patent is extended or adjusted under 35 U.S.C. 154(b) by 264 days.

This patent is subject to a terminal disclaimer.

(21) Appl. No.: 18/099,481

(22) Filed: Jan. 20, 2023

(65) Prior Publication Data

US 2023/0149018 A1    May 18, 2023

Related U.S. Application Data

(63) Continuation of application No. 17/733,387, filed on Apr. 29, 2022, now Pat. No. 11,583,280.
(Continued)

(51) Int. Cl.
*A61B 17/11* (2006.01)
*A61B 17/00* (2006.01)

(52) U.S. Cl.
CPC . *A61B 17/1114* (2013.01); *A61B 2017/00004* (2013.01); *A61B 2017/00876* (2013.01); *A61B 2017/1139* (2013.01)

(58) Field of Classification Search
None
See application file for complete search history.

(56) References Cited

U.S. PATENT DOCUMENTS 6,632,229 B1   10/2003  Yamanouchi
6,719,768 B1    4/2004  Cole et al.
(Continued)

FOREIGN PATENT DOCUMENTS

EP    1493391 B1   12/2009
EP    2207488 B1    9/2012
(Continued)

OTHER PUBLICATIONS

International Search Report & Written Opinion, International Patent Application No. PCT/US2022/027009, mailed Oct. 5, 2022, 18 pages.

*Primary Examiner* — Shaun L David
(74) *Attorney, Agent, or Firm* — Casimir Jones, S.C.; Robert A. Goetz

(57) ABSTRACT

Systems and methods for forming an anastomosis between two adjacent walls of a digestive tract are provided. The system can include first and second magnetic implants configured to magnetically couple through two adjacent walls of the digestive tract to compress a portion of the two adjacent walls therebetween and form a necrotic area that becomes surrounded by a scarred edge following a healing time period. The magnetic implant can include a magnetic member and a non-magnetic member. The system can include a retention member extending outwardly from a corresponding one of the first and second magnetic implants, the retention member being configured to retain the magnetic implants in position and prevent passage thereof through the necrotic area during the healing time period, and to maintain an engagement between the magnetic member and the non-magnetic member during the healing time period and enable disengagement thereof following the healing time period.

21 Claims, 15 Drawing Sheets

Related U.S. Application Data

(60) Provisional application No. 63/201,474, filed on Apr. 30, 2021.

(56) References Cited

U.S. PATENT DOCUMENTS

| | | | |
|---|---|---|---|
| 7,282,057 B2 | 10/2007 | Surti et al. |
| 7,909,837 B2 | 3/2011 | Crews et al. |
| 8,043,290 B2 | 10/2011 | Harrison et al. |
| 8,262,680 B2 | 9/2012 | Swain et al. |
| 8,506,516 B2 | 8/2013 | Kassab et al. |
| 8,556,919 B2 | 10/2013 | Aguirre et al. |
| 8,623,036 B2 | 1/2014 | Harrison et al. |
| 8,679,139 B2 | 3/2014 | Aguirre et al. |
| 8,685,046 B2 | 4/2014 | Viola |
| 8,728,105 B2 | 5/2014 | Aguirre et al. |
| 8,794,243 B2 | 8/2014 | Deem et al. |
| 8,828,031 B2 | 9/2014 | Fox et al. |
| 8,845,663 B2 | 9/2014 | Chmura |
| 8,915,915 B2 | 12/2014 | Harrison et al. |
| 9,168,041 B2 | 10/2015 | Zaritsky et al. |
| 9,226,753 B2 | 1/2016 | Surti et al. |
| 9,456,820 B2 | 10/2016 | Gagner et al. |
| 9,943,335 B2 | 4/2018 | Gittard et al. |
| 10,039,550 B2 | 8/2018 | Altman |
| 10,182,821 B2 | 1/2019 | Lukin et al. |
| 10,285,703 B2 | 5/2019 | Viola |
| 10,342,544 B2 | 7/2019 | Bakos et al. |
| 10,376,400 B2 | 8/2019 | Mcguckin, Jr. |
| 10,448,954 B2 | 10/2019 | Mcweeney et al. |
| 10,555,735 B2 | 2/2020 | Bakos et al. |
| 10,568,630 B2 | 2/2020 | Hernandez et al. |
| 10,624,643 B2 | 4/2020 | Hunt et al. |
| 10,624,644 B2 | 4/2020 | Bakos et al. |
| 10,631,865 B2 | 4/2020 | Bakos et al. |
| 10,682,143 B2 | 6/2020 | Hernandez et al. |
| 10,779,831 B2 | 9/2020 | Lukin et al. |
| 10,813,642 B2 | 10/2020 | Beisel et al. |
| 10,952,732 B2 | 3/2021 | Binmoeller et al. |
| 2008/0114384 A1 | 5/2008 | Chang et al. |
| 2009/0227828 A1* | 9/2009 | Swain ................ A61B 17/1114 600/12 |
| 2015/0057687 A1 | 2/2015 | Gittard et al. |
| 2016/0287257 A1 | 10/2016 | Fabian et al. |
| 2017/0265866 A1 | 9/2017 | Ryou et al. |
| 2018/0028186 A1 | 2/2018 | Yamanouchi |
| 2018/0296218 A1 | 10/2018 | Binmoeller et al. |
| 2019/0133678 A1 | 5/2019 | Pate et al. |
| 2019/0183507 A1 | 6/2019 | Baillargeon |
| 2019/0261998 A1 | 8/2019 | Altman et al. |
| 2019/0274687 A1 | 9/2019 | Wang et al. |
| 2020/0008834 A1 | 1/2020 | Cauche et al. |
| 2020/0129283 A1 | 4/2020 | Swensgard et al. |
| 2020/0138438 A1 | 5/2020 | Harrison et al. |
| 2020/0246009 A1 | 8/2020 | Gagner et al. |
| 2020/0323530 A1 | 10/2020 | Sharma |
| 2022/0087678 A1 | 3/2022 | Gagner et al. |

FOREIGN PATENT DOCUMENTS

| | | |
|---|---|---|
| EP | 2538852 A1 | 1/2013 |
| EP | 3267905 A1 | 1/2018 |
| EP | 2260752 B1 | 3/2018 |
| EP | 3573542 A1 | 12/2019 |
| EP | 3487418 A4 | 4/2020 |
| WO | WO2014055193 A1 | 4/2014 |
| WO | WO2016082481 A1 | 6/2016 |
| WO | WO2019077218 A1 | 4/2019 |
| WO | WO2019232526 A1 | 6/2019 |
| WO | WO2019232527 A1 | 12/2019 |
| WO | WO 2021/207821 | 10/2021 |

* cited by examiner

ANASTOMOSIS FORMATION WITH MAGNETIC DEVICES HAVING BIORESORBABLE RETENTION MEMBER

CROSS-REFERENCE TO RELATED APPLICATION

The present application is a continuation of U.S. patent application Ser. No. 17/733,387, filed Apr. 29, 2022, which claims priority from U.S. provisional patent application No. 63/201,474, filed on Apr. 30, 2021, and entitled "ANASTOMOSIS FORMATION WITH MAGNETIC DEVICES HAVING BIORESORBABLE RETENTION MEMBER", the disclosure of which is hereby incorporated by reference in its entirety.

TECHNICAL FIELD

The technical field generally relates to medical techniques for treating digestive tract and obesity conditions. In particular, the technical field relates to medical techniques including devices for forming an anastomosis in the digestive tract.

BACKGROUND

Metabolic surgeries and medical procedures to treat conditions associated with the digestive tract, diabetes and obesity often require alteration of the digestive tract through incisions, sutures, punctures and/or stapling, which can cause trauma to the organ being altered and lead to bleeding. For instance, bariatric surgery procedures can be used to treat obesity, and can be aimed at bypassing a portion of the stomach and/or the intestine. Such medical procedures can also lead to an increased risk of infection or other complications.

Magnetic compression anastomosis can be used in the context of medical procedures to treat conditions associated with the digestive tract. With magnetic compression anastomosis, necrosis is induced in tissue sandwiched between two magnets. A healing process takes place around the magnets, while the compressed tissue eventually dies and separates from surrounding living tissue. The magnets are released along with the necrotic tissue, leaving an open passage known as an anastomosis. There are challenges related to the formation of anastomoses, particularly larger anastomoses, in the digestive tract.

There remain a number of challenges with respect to surgery procedures in the digestive tract, particularly in the formation of an anastomosis.

SUMMARY

In accordance with an aspect, there is provided a system for forming an anastomosis between two adjacent walls of a digestive tract, the system comprising:
first and second magnetic implants configured to magnetically couple to each other through the two adjacent walls of the digestive tract to compress a portion of the two adjacent walls therebetween and form a necrotic area that becomes surrounded by a scarred edge following a healing time period, each one of the magnetic implant comprising:
a magnetic member comprising a magnet; and
a non-magnetic member provided in a longitudinally adjacent relationship relative to the magnetic member; and
a retention member extending outwardly from a corresponding one of the first and second magnetic implants, the retention member being configured to temporarily retain the magnetic member and the non-magnetic member engaged together during the healing time period.

In some implementations, the non-magnetic member comprises two non-magnetic members, one of the two non-magnetic members being provided at one longitudinal end of the magnetic member and another one of the two non-magnetic members being provided at another longitudinal end of the magnetic member.

In some implementations, each one of the first and second magnetic implants has an effective length, and the magnetic member has a length that represents at least 50% of the effective length.

In some implementations, each one of the first and second magnetic implants has an effective length, and the magnetic member has a length that represents between 50% and 80% of the effective length.

In some implementations, each one of the first and second magnetic implants has an effective length, and the magnetic member has a length that represents at least 70% of the effective length.

In some implementations, the magnetic member and the non-magnetic member are engaged together via a male-female engagement.

In some implementations, the magnetic member comprises a non-magnetic member receiving cavity and the non-magnetic member comprises a non-magnetic member projection, the non-magnetic member receiving cavity being sized and configured for receiving the non-magnetic member projection therein.

In some implementations, the non-magnetic member comprises a magnetic member receiving cavity and the magnetic member comprises a magnetic member projection, the magnetic member receiving cavity being sized and configured for receiving the magnetic member projection therein.

In some implementations, the male-female engagement is configured to transfer a bending load resulting from the magnetic coupling of the magnetic member of each one of the first and second magnetic implants to the non-magnetic member.

In some implementations, the male-female engagement is configured for limiting a rotational movement of the non-magnetic member relative to the magnetic member, in an upward or downward direction relative to a transverse axis of the non-magnetic member.

In some implementations, the retention member is configured for maintaining the male-female engagement during the healing time period.

In some implementations, the retention member at least spans a transition from the magnetic member to the non-magnetic member.

In some implementations, the retention member is configured for limiting a movement of the non-magnetic member relative to the magnetic member.

In some implementations, the movement is a translational movement.

In some implementations, the magnetic member further comprises a housing configured to house the magnet therein.

In some implementations, the magnetic member further comprises a housing, and the magnet comprises multiple magnets housed in the housing.

In some implementations, the housing of the magnetic member fully encloses the magnet therein.

In some implementations, the non-magnetic member includes two halves.

In some implementations, the non-magnetic member is made of a single component.

In some implementations, each one of the magnetic member and the non-magnetic member of the first and second magnetic implants comprises a lumen-oriented portion and a tissue-contacting portion.

In some implementations, the lumen-oriented portion of at least one of the first and second magnetic implants comprises a flat compression surface.

In some implementations, the lumen-oriented portion of each one of the first and second magnetic implants comprises a flat compression surface.

In some implementations, the lumen-oriented portion of at least one of the first and second magnetic implants comprises furrows.

In some implementations, the retention member comprises first and second longitudinal members, each one of the first and second longitudinal members extending longitudinally along a longitudinal axis of a corresponding one of the first and second magnetic implants, and being provided around an outer periphery of the corresponding one of the first and second magnetic implants.

In some implementations, each one of the first and second longitudinal members comprises a flange.

In some implementations, the retention member further comprises a plurality of struts provided in a spaced-apart relationship and extending inwardly from a corresponding one of the first and second longitudinal members toward the outer periphery of the corresponding one of the first and second magnetic implants.

In some implementations, the non-magnetic member comprises a non-magnetic member flange at a distal portion thereof.

In some implementations, the non-magnetic member flange is integral with the non-magnetic member.

In some implementations, the flange and the non-magnetic member flange together extend substantially continuously and circumferentially around the corresponding one of the first and second magnetic implants.

In some implementations, the housing comprises a first set of strut-engaging openings sized and configured to receive therein a first set of the plurality of struts of the retention member.

In some implementations, the non-magnetic member comprises a second set of strut-engaging openings sized and configured to receive therein a second set of the plurality of struts of the retention member.

In some implementations, the retention member further comprises a runner provided inwardly from the plurality of struts, the plurality of struts extending between the corresponding one of the first and second longitudinal members and the runner.

In some implementations, the housing further comprises a housing runner-receiving portion sized and configured to enable abutment of a first portion of the runner thereon.

In some implementations, the non-magnetic member further comprises a non-magnetic member runner-receiving portion sized and configured to enable abutment of a second portion of the runner thereon.

In some implementations, the magnetic member runner-receiving portion comprises a groove.

In some implementations, the non-magnetic member further comprises a connecting member connectable to a connector extending from a corresponding endoscope to be releasably engageable with the connector.

In some implementations, the connector is a delivery catheter.

In some implementations, the connecting member comprises a delivery catheter attachment assembly connectable to the delivery catheter.

In some implementations, the retention member is discrete from the housing.

In some implementations, the retention member and the housing are made of a different material.

In some implementations, the retention member and the non-magnetic member are made of a same material.

In some implementations, the retention member and the non-magnetic member are made of a different material.

In some implementations, the retention member and the housing are manufactured in a different manufacturing process.

In some implementations, the retention member is attachable, engageable, or couplable to the housing following the different manufacturing process.

In some implementations, the retention member comprises at least one of a bioerodible material, a biodegradable material, and a bioresorbable material.

In some implementations, the retention member comprises a synthetic aliphatic polyester.

In some implementations, the retention member comprises at least one of polylactic acid, polyglycolic acid, polylactic-co-glycolic acid, polycaprolactone, and polydioxanone.

In some implementations, the retention member is made of a combination of poly-hydroxyacetic ester, lactide copolymers and glycolic/lactide copolymers (PLGA).

In some implementations, the retention member comprises at least two materials, the at least two materials having a different dissolution rate or a different degradation rate once implanted in a given environment.

In some implementations, the retention member comprises at least one notch or spot having a dissolution rate or a degradation rate that is different from a remainder thereof once implanted in a given environment.

In some implementations, the retention member of the first and second magnetic implants is made of a same material.

In some implementations, the retention member of the first magnetic implant is made from a different material than the retention member of the second magnetic implant.

In some implementations, the first magnetic implant is configured for implantation in a strongly acidic environment and the second magnetic implant is configured for implantation in a weakly acidic environment, and once implanted in the strong acidic environment and in the weak acidic environment respectively, the retention member of the first and second magnetic implants have a similar dissolution rate or degradation rate.

In some implementations, the non-magnetic member comprises polydimethylsiloxane or a fluoropolymer.

In some implementations, the non-magnetic member comprises a titanium alloy, cobalt chromium, or an austenitic stainless steel.

In some implementations, the retention member of the first magnetic implant and the retention member of the second magnetic implant have a same configuration.

In some implementations, the retention member of the first magnetic implant and the retention member of the second magnetic implant have a different configuration.

In some implementations, the retention member is rigid.

In some implementations, the retention member is defeatable following the healing time period.

In some implementations, the retention member is defeatable via a dissolution mechanism or a degradation mechanism.

In some implementations, the retention member extends outwardly from the corresponding one of the first and second magnetic implants at a right angle.

In some implementations, the retention member extends outwardly from the corresponding one of the first and second magnetic implants at an obtuse angle.

In some implementations, the retention member extends outwardly from the corresponding one of the first and second magnetic implants at an acute angle.

In some implementations, the retention member has a T-shape configuration.

In some implementations, the retention members of the first and second magnetic implants are configured such that the implant remain within the digestive tract for at least about one week, at least about 2 weeks or for about 2 weeks to about 4 weeks.

In accordance with another aspect, there is provided a system for forming an anastomosis between two adjacent walls of a digestive tract, the system comprising:
  first and second magnetic implants configured to magnetically couple to each other through the two adjacent walls of the digestive tract to compress a portion of the two adjacent walls therebetween and form a necrotic area that becomes surrounded by a scarred edge following a healing time period;
    a magnetic member comprising a magnet; and
    a non-magnetic member provided in a longitudinally adjacent relationship relative to the magnetic member; and
  a retention member extending outwardly from at least one of the first and second magnetic implants, the retention member being configured to temporarily retain the magnetic member and the non-magnetic member together during the healing time period.

In some implementations, the system further comprises one or more features as defined herein.

In accordance with another aspect, there is provided a method for forming an anastomosis between two adjacent walls of a digestive tract of a patient, the method comprising:
  navigating a first magnetic implant into the digestive tract to a first location on one side of a desired anastomose site;
  delivering a second magnetic implant into the digestive tract to a second location on another side of the desired anastomose site;
  wherein the first and second magnetic implants each comprises a magnetic member and a non-magnetic member provided in a longitudinally adjacent relationship;
  magnetically coupling the magnetic member of each one of the first and second magnetic implants together through the two adjacent vessel walls of the digestive tract to compress a portion of the two adjacent walls between the first and second magnetic implants and form a necrotic area;
  retaining the first and second magnetic implants in position on respective sides of the two adjacent walls during a healing time period to enable formation of a scarred edge that surrounds the necrotic area;
  retaining the magnetic member and the non-magnetic member engaged together during the healing time period; and
  after completion of the healing time period, disengaging the magnetic member and the non-magnetic member of at least one of first and second magnetic implants from each other.

In some implementations, retaining the first and second magnetic implants in position on respective sides of the two adjacent walls comprises providing a retention member extending outwardly from each one of the first and second magnetic implants to prevent passage thereof through the necrotic area.

In some implementations, retaining the magnetic member and the non-magnetic member engaged together during the healing time period is performed via the retention member.

In some implementations, disengaging the magnetic member and the non-magnetic member comprises defeating at least a portion of the retention member.

In some implementations, defeating at least a portion of the retention member is performed via at least one of a chemical mechanism and a mechanical mechanism.

In some implementations, navigating the first magnetic implant to the first location comprises releasably engaging the first magnetic implant with a corresponding delivery catheter insertable in a working channel of a corresponding endoscope via a connecting member.

In some implementations, delivering the second magnetic implant to a second location comprises engaging the second magnetic implant with a laparoscopic device.

In some implementations, the method further comprises passing the magnetically coupled magnetic members of the first and second magnetic implants separately from the non-magnetic member of each one of the first and second magnetic implants after the healing time period is completed.

In some implementations, the method further comprises one or more features as defined herein.

In accordance with another aspect, there is provided a method for forming an anastomosis between two adjacent walls of a digestive tract of a patient, the method comprising:
  magnetically coupling a magnetic member of a first and second magnetic implants together through the two adjacent vessel walls of the digestive tract to compress a portion of the two adjacent walls between the first and second magnetic implants and form a necrotic area, each one of the first and second magnetic implants further comprising a non-magnetic member provided in a longitudinally adjacent relationship relative to the magnetic member;
  retaining the first and second magnetic implants in position on respective sides of the two adjacent walls during a healing time period to enable formation of a scarred edge that surrounds the necrotic area;
  retaining the magnetic member and the non-magnetic member engaged together during the healing time period; and
  after completion of the healing time period, disengaging the magnetic member and the non-magnetic member of at least one of first and second magnetic implants from each other.

In some implementations, the method further comprises one or more features as defined herein.

In accordance with another aspect, there is provided a system for forming an anastomosis between two adjacent walls of a digestive tract, the system comprising:
  first and second magnetic implants configured to magnetically couple to each other through the two adjacent walls of the digestive tract to compress a portion of the two adjacent walls therebetween and form a necrotic area that becomes surrounded by a scarred edge following a healing time period, each one of the magnetic implant comprising:
a magnetic member comprising a magnet;
a non-magnetic member provided in a longitudinally adjacent relationship relative to the magnetic member; and
a defeatable portion located between the magnetic member and the non-magnetic member, the defeatable portion being configured to temporarily retain the magnetic member and the non-magnetic member engaged together during the healing time period.

In some implementations, the defeatable portion is thinner than a thickness of the magnetic member.

In some implementations, the defeatable portion is narrower than a width of the magnetic member.

In some implementations, the defeatable portion includes a plurality of struts.

In some implementations, the defeatable portion includes a plurality of regions having a reduced thickness compared to a thickness of the magnetic member.

In some implementations, the defeatable portion comprises at least one of a bioerodible material, a biodegradable material, and a bioresorbable material.

In some implementations, the defeatable portion comprises a synthetic aliphatic polyester.

In some implementations, the defeatable portion comprises at least one of polylactic acid, polyglycolic acid, polylactic-co-glycolic acid, polycaprolactone, and polydioxanone.

In some implementations, the defeatable portion is made of a combination of poly-hydroxyacetic ester, lactide copolymers and glycolic/lactide copolymers (PLGA).

In some implementations, the defeatable portion comprises at least two materials, the at least two materials having a different dissolution rate or a different degradation rate once implanted in a given environment.

In some implementations, the defeatable portion comprises at least one notch or spot having a dissolution rate or a degradation rate that is different from a remainder thereof once implanted in a given environment.

In some implementations, the defeatable portions of the first and second magnetic implants are made of a same material.

In some implementations, the defeatable portion of the first magnetic implant is made from a different material than the defeatable portion of the second magnetic implant.

In some implementations, the first magnetic implant is configured for implantation in a strongly acidic environment and the second magnetic implant is configured for implantation in a weakly acidic environment, and once implanted in the strong acidic environment and in the weak acidic environment respectively, the defeatable portion of the first and second magnetic implants have a similar dissolution rate or degradation rate.

In some implementations, the non-magnetic member comprises polydimethylsiloxane or a fluoropolymer.

In some implementations, the non-magnetic member comprises a titanium alloy, cobalt chromium, or an austenitic stainless steel.

In some implementations, the defeatable portion is defeatable via a dissolution mechanism or a degradation mechanism.

In some implementations, the non-magnetic member comprises two non-magnetic members, one of the two non-magnetic members being provided at one longitudinal end of the magnetic member and another one of the two non-magnetic members being provided at another longitudinal end of the magnetic member.

In some implementations, each one of the first and second magnetic implants has an effective length, and the magnetic member has a length that represents at least 50% of the effective length.

In some implementations, each one of the first and second magnetic implants has an effective length, and the magnetic member has a length that represents between 50% and 80% of the effective length.

In some implementations, each one of the first and second magnetic implants has an effective length, and the magnetic member has a length that represents at least 70% of the effective length.

In some implementations, the magnetic member further comprises a housing configured to house the magnet therein.

In some implementations, the magnetic member further comprises a housing, and the magnet comprises multiple magnets housed in the housing.

In some implementations, the housing of the magnetic member fully encloses the magnet therein.

In some implementations, the non-magnetic member includes two halves.

In some implementations, the non-magnetic member is made of a single component.

In some implementations, each one of the magnetic member and the non-magnetic member of the first and second magnetic implants comprises a lumen-oriented portion and a tissue-contacting portion.

In some implementations, the lumen-oriented portion of at least one of the first and second magnetic implants comprises a flat compression surface.

In some implementations, the lumen-oriented portion of each one of the first and second magnetic implants comprises a flat compression surface.

In some implementations, the lumen-oriented portion of at least one of the first and second magnetic implants comprises furrows.

In some implementations, the non-magnetic member further comprises a connecting member connectable to a connector extending from a corresponding endoscope to be releasably engageable with the connector.

In some implementations, the connector is a delivery catheter.

In some implementations, the connecting member comprises a delivery catheter attachment assembly connectable to the delivery catheter.

In some implementations, the healing time period is at least about 3 days, at least one week, at least two weeks, or between about 2 weeks to about 4 weeks.

In some implementations, the system further comprises one or more features as defined herein.

In accordance with another aspect, there is provided a system for forming an anastomosis between two adjacent walls of a digestive tract, the system comprising:
first and second magnetic implants configured to magnetically couple to each other through the two adjacent walls of the digestive tract to compress a portion of the two adjacent walls therebetween and form a necrotic area that becomes surrounded by a scarred edge following a healing time period, each one of the magnetic implant comprising:
a magnetic member comprising a magnet, the magnetic member having an outer periphery;

a non-magnetic member provided along at least a portion of the outer periphery of the magnetic member; and a defeatable portion configured to temporarily retain the magnetic member and the non-magnetic member engaged together during the healing time period.

In some implementations, the non-magnetic member comprises a first and second non-magnetic members, a first one of the non-magnetic members being provided at one longitudinal end of the magnetic member and a second one of the non-magnetic members being provided at another longitudinal end of the magnetic member.

In some implementations, each one of the magnetic member and the non-magnetic member of the first and second magnetic implants comprises a lumen-oriented portion and a tissue-contacting portion.

In some implementations, the defeatable portion is provided on the lumen-oriented portion of a respective one of the first and second magnetic implants and spans transition from the magnetic member to the two non-magnetic member.

In some implementations, the defeatable portion comprises a first and second defeatable portions provided on the lumen-oriented portion of a respective one of the first and second magnetic implants, the first defeatable portion spanning a transition from the first non-magnetic member to the magnetic member and the second defeatable portion spanning a transition from the second non-magnetic member to the magnetic member.

In some implementations, the defeatable portion is provided between the magnetic member and the non-magnetic member.

In some implementations, the non-magnetic member comprises a first and second non-magnetic members, a first one of the non-magnetic members being provided on one lateral side of the magnetic member and a second one of the non-magnetic members being provided on another lateral side of the magnetic member, the first and second non-magnetic members being retained together via the defeatable portion.

In some implementations, the defeatable portion is thinner than a thickness of the magnetic member.

In some implementations, the defeatable portion is narrower than a width of the magnetic member.

In some implementations, the defeatable portion includes a plurality of struts.

In some implementations, the defeatable portion includes regions having a reduced thickened compared to a thickness of the magnetic member.

In some implementations, the defeatable portion comprises at least one of a bioerodible material, a biodegradable material, and a bioresorbable material.

In some implementations, the defeatable portion comprises a synthetic aliphatic polyester.

In some implementations, the defeatable portion comprises at least one of polylactic acid, polyglycolic acid, polylactic-co-glycolic acid, polycaprolactone, and polydioxanone.

In some implementations, the defeatable portion is made of a combination of poly-hydroxyacetic ester, lactide copolymers and glycolic/lactide copolymers (PLGA).

In some implementations, the defeatable portion comprises at least two materials, the at least two materials having a different dissolution rate or a different degradation rate once implanted in a given environment.

In some implementations, the defeatable portion comprises at least one notch or spot having a dissolution rate or a degradation rate that is different from a remainder thereof once implanted in a given environment.

In some implementations, the defeatable portions of the first and second magnetic implants are made of a same material.

In some implementations, the defeatable portion of the first magnetic implant is made from a different material than the defeatable portion of the second magnetic implant.

In some implementations, the first magnetic implant is configured for implantation in a strongly acidic environment and the second magnetic implant is configured for implantation in a weakly acidic environment, and once implanted in the strong acidic environment and in the weak acidic environment respectively, the defeatable portion of the first and second magnetic implants have a similar dissolution rate or degradation rate.

In some implementations, the non-magnetic member comprises polydimethylsiloxane or a fluoropolymer.

In some implementations, the non-magnetic member comprises a titanium alloy, cobalt chromium, or an austenitic stainless steel.

In some implementations, the defeatable portion is defeatable via a dissolution mechanism or a degradation mechanism.

In some implementations, the magnetic member further comprises a housing configured to house the magnet therein.

In some implementations, the magnetic member further comprises a housing, and the magnet comprises multiple magnets housed in the housing.

In some implementations, the housing of the magnetic member fully encloses the magnet therein.

In some implementations, the non-magnetic member includes two halves.

In some implementations, the non-magnetic member is made of a single component.

In some implementations, the non-magnetic member further comprises a connecting member connectable to a connector extending from a corresponding endoscope to be releasably engageable with the connector.

In some implementations, the connector is a delivery catheter.

In some implementations, the connecting member comprises a delivery catheter attachment assembly connectable to the delivery catheter.

In some implementations, the healing time period is at least about 3 days, at least one week, at least two weeks, or between about 2 weeks to about 4 weeks.

In some implementations, the system further comprises one or more features as defined herein.

In accordance with another aspect, there is provided a system for forming an anastomosis between two adjacent walls of a digestive tract, the system comprising:

a first magnetic implant comprising a first magnet and being implantable in a duodenum; and a second magnetic implant comprising a second magnet and being implantable in an ileum;

the first and second magnetic implants being configured to magnetically couple to each other through the two adjacent walls of the duodenum and ileum to compress a portion of the two adjacent walls therebetween and form a necrotic area that becomes surrounded by a scarred edge following a healing time period; and the first and second magnetic implants each having a length to width ratio of more than 1:1 and less than 4:1.

In some implementations, the length to width ratio of the first and second magnetic implants ranges between 1.5:1 and 4:1.

In some implementations, the length to width ratio of the first and second magnetic implants ranges between 2:1 and 4:1.

In some implementations, at least one of the first and second magnetic implants further comprises a housing configured to house a corresponding one of the first and second magnets therein.

In some implementations, each one of the first and second magnetic implants comprises a lumen-oriented portion and a tissue-contacting portion.

In some implementations, the lumen-oriented portion of at least one of the first and second magnetic implants comprises a flat compression surface.

In some implementations, the lumen-oriented portion of each one of the first and second magnetic implants comprises a flat compression surface.

In some implementations, the lumen-oriented portion of at least one of the first and second magnetic implants comprises furrows.

In some implementations, at least one of the first and second magnetic implants further comprises a connecting member connectable to a connector extending from a corresponding endoscope to be releasably engageable with the connector.

In some implementations, the connector is a delivery catheter.

In some implementations, the connecting member comprises a delivery catheter attachment assembly connectable to the delivery catheter.

In some implementations, the system further comprises one or more features as defined herein.

In accordance with another aspect, there is provided a system for forming an anastomosis between two adjacent walls of a digestive tract, the system comprising:
  first and second magnetic implants configured to magnetically couple to each other through the two adjacent walls of the digestive tract to compress a portion of the two adjacent walls therebetween and form a necrotic area that becomes surrounded by a scarred edge following a healing time period, each one of the first and second magnetic implants comprising:
    a magnetic member comprising a magnet; and
    a non-magnetic member provided in a longitudinally adjacent relationship relative to the magnetic member; and
  a retention member extending outwardly from at least one of the first and second magnetic implants, the retention member being configured to temporarily retain the magnetic member and the non-magnetic member of the at least one of the first and second magnetic implants engaged together during the healing time period.

In some implementations, the non-magnetic member comprises first and second magnetic members, the first non-magnetic member being provided at a first longitudinal end of the magnetic member and the second non-magnetic member being provided at a second longitudinal end of the magnetic member.

In some implementations, the magnetic member and the non-magnetic member are engaged together via a male-female engagement, and the retention member at least spans a transition from the magnetic member to the non-magnetic member.

In some implementations, the retention member comprises first and second longitudinal members, each one of the first and second longitudinal members extending longitudinally along a longitudinal axis of the at least one of the first and second magnetic implants, and being provided around a portion of an outer periphery of the at least one of the first and second magnetic implants.

In some implementations, the retention member further comprises a plurality of struts provided in a spaced-apart relationship and extending inwardly from a corresponding one of the first and second longitudinal members toward the portion of the outer periphery of the at least one of the first and second magnetic implants.

In some implementations, the non-magnetic member comprises a non-magnetic member flange at a distal portion thereof.

In some implementations, the non-magnetic member flange is integral with the non-magnetic member.

In some implementations, the non-magnetic member includes two halves.

In some implementations, the magnetic member further comprises a housing configured to house the magnet therein.

In some implementations, the housing comprises a first set of strut-engaging openings sized and configured to receive therein a first set of the plurality of struts of the retention member, the non-magnetic member comprises a second set of strut-engaging openings sized and configured to receive therein a second set of the plurality of struts of the retention member, and the retention member further comprises a runner provided inwardly from the plurality of struts, the plurality of struts extending between the corresponding one of the first and second longitudinal members and the runner.

In some implementations, the housing further comprises a housing runner-receiving portion sized and configured to enable abutment of a first portion of the runner thereon, and the non-magnetic member further comprises a non-magnetic member runner-receiving portion sized and configured to enable abutment of a second portion of the runner thereon.

In some implementations, the retention member and the housing are made of a different material.

In some implementations, the retention member and the non-magnetic member are made of a same material.

In some implementations, the retention member and the non-magnetic member are made of a different material.

In some implementations, the retention member comprises at least one of a bioerodible material, a biodegradable material, and a bioresorbable material.

In some implementations, the retention member comprises at least two materials, the at least two materials having a different dissolution rate or a different degradation rate once implanted in a given environment.

In some implementations, the retention member comprises at least one notch or spot having a dissolution rate or a degradation rate that is different from a remainder thereof once implanted in a given environment.

In some implementations, the retention member is defeatable following the healing time period.

In some implementations, the retention member is defeatable via a dissolution mechanism or a degradation mechanism.

In accordance with another aspect, there is provide a system for forming an anastomosis between two adjacent walls of a digestive tract, the system comprising:
  first and second magnetic implants configured to magnetically couple to each other through the two adjacent walls of the digestive tract to compress a portion of the two adjacent walls therebetween and form a necrotic area that becomes surrounded by a scarred edge following a healing time period, at least one of the first and second magnetic implants comprising:

a magnetic member comprising a magnet;
a non-magnetic member provided in a longitudinally adjacent relationship relative to the magnetic member; and
a defeatable portion located between the magnetic member and the non-magnetic member, the defeatable portion being configured to temporarily retain the magnetic member and the non-magnetic member engaged together during the healing time period.

In some implementations, the defeatable portion is thinner than a thickness of the magnetic member or narrower than a width of the magnetic member.

In some implementations, the defeatable portion includes a plurality of struts.

In some implementations, the defeatable portion includes a plurality of regions having a reduced thickness compared to a thickness of the magnetic member.

In some implementations, the defeatable portion comprises at least one of a bioerodible material, a biodegradable material, and a bioresorbable material.

In some implementations, the defeatable portion comprises at least two materials, the at least two materials having a different dissolution rate or a different degradation rate once implanted in a given environment.

In some implementations, the defeatable portion comprises at least one notch or spot having a dissolution rate or a degradation rate that is different from a remainder thereof once implanted in a given environment.

In some implementations, the non-magnetic member comprises first and second magnetic members, the first non-magnetic member being provided at a first longitudinal end of the magnetic member and the second non-magnetic member being provided at a second longitudinal end of the magnetic member, and the defeatable portion comprising a first defeatable portion between the first non-magnetic member and the magnetic member and a second defeatable portion between the second non-magnetic member and the magnetic member.

In some implementations, the magnetic member further comprises a housing configured to house the magnet therein.

In some implementations, the non-magnetic member includes two halves.

BRIEF DESCRIPTION OF THE DRAWINGS

The attached figures illustrate various features, aspects and implementations of the technology described herein.

FIG. 14B is a side view of the first and second magnetic implants shown in FIG. 14a.

FIG. 21F is a top view of a magnetic implant in accordance with another implementation, the magnetic implant comprising a magnetic member and a non-magnetic member that surrounds the magnetic member, with a defeatable portion in between.

DETAILED DESCRIPTION

Figure 1:
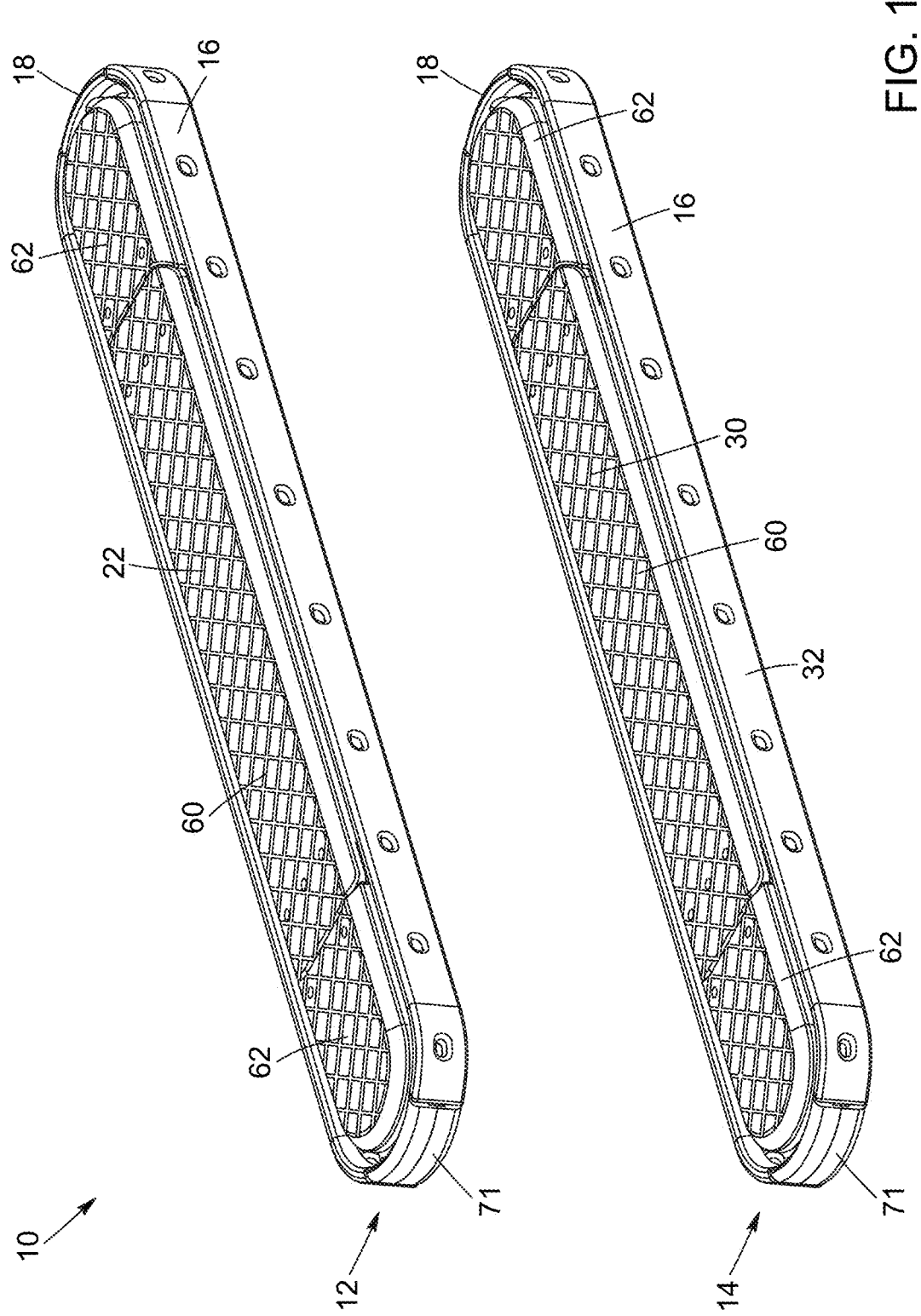
FIG. 1 is a perspective view of first and second magnetic implants in accordance with an implementation, each magnetic implant comprising a magnetic member, first and second non-magnetic members, and a retention member.

Techniques described herein relate to systems, devices and methods for forming an anastomosis between two adjacent walls of hollow structures of the digestive tract of a patient, in the context of procedures to treat various medical conditions associated with the digestive tract.

The formation of the anastomosis can be achieved without puncturing the tissue of the hollow structures through which the anastomosis is formed, for example by inserting a first magnetic implant into the lumen of a first hollow organ and a second magnetic implant into the lumen of a second hollow organ, positioning the first and second magnetic implants at a desired anastomosis site, and by magnetically coupling the first and second magnetic implants together to compress the tissue of the adjacent walls therebetween. Compression of the wall tissue between the two magnetic implants results in a necrotic area that corresponds approximately to the surface area of the compression surface of the magnetic implant pair. Over time, the necrotic area becomes surrounded by an edge of scar tissue, or scarred edge. The formation of scar tissue can include collagen fiber deposition, neovascularization, and epithelial regeneration, and represents a dynamic equilibrium involving cells, their milieu, and the extracellular matrix. Cytokines secreted by platelets and inflammatory cells can promote the formation of new blood vessels and collagen synthesis which, in dynamic balance with collagen degradation, can contribute to determine the healing response. Two components of collagen are hydroxyproline and hydroxylysine, with hydroxyproline being synthesized under conditions of oxidative stress via the hydroxylation of proline, and being involved in the cellular transport of collagen. The synthesis and transport of wound collagen can thus be understood by monitoring the hydroxyproline content of the wound. The edge of scar tissue can thus be characterized by the fusion, or mechanical bonding, of the walls of each hollow organ through which the anastomosis is formed that occurs in part via fibrosis mechanisms. The scarred edge can thus form a fluid-tight seal around the anastomosis.

To facilitate maintaining the pair of magnetic implants in place for a sufficient period of time to enable formation of the scarred edge and prevent premature passage of the pair of magnetic implants through the necrotic area, at least one of the magnetic implants can include a retention member that extends outwardly from the corresponding magnetic implant. The retention member described in the present description can be any structure that is temporarily coupled to the magnetic implant or that temporarily forms part of the magnetic implant, and is configured to prevent or inhibit the pair of magnetic implants from prematurely passing through the necrotic area, i.e., prior to an edge healing time period being completed, such that the magnetic implants and necrotic tissue are released only after good scar formation is complete. For example, the retention member can include a flange or extension, provided continuously or discontinuously around the periphery of the magnetic implant, e.g., around the peripheral wall of the magnetic implant. The retention member can also take several other forms and can include various features, for instance with regard to the materials of which the retention member is made, geometric characteristics, configurations, and so on. Each of the magnetic implants can include a corresponding retention member such that the magnetically coupled pair of implants is prevented from passing through the necrotic region in both directions during the healing time period.

The retention member can adopt a modifiable configuration over time, to achieve various purposes. For instance, the retention member can be made of a bioresorbable material that loses its mechanical properties and/or disintegrates after a given period of time, which can correspond to a timepoint during the healing time period, or a timepoint after the healing time period is completed.

To create an anastomosis having a large diameter, for instance when creating an anastomosis between a wall of the stomach and the jejunum, the magnetic implant can include a magnetic member that can be a magnet, or that can include a magnet received in a housing, and at least one non-magnetic member provided in a longitudinally adjacent relationship relative to the magnetic member. The magnetic member and the non-magnetic member are engaged with each other to provide a magnetic implant having a longer effective length than the length of the magnetic member as an individual component. Given that the length of the magnetic implant is directly related to the diameter of the resulting anastomosis, a longer magnetic implant can thus enable creating anastomosis having a large diameter. In implementations where the magnetic implant includes a magnetic member and a least one non-magnetic member, the retention member is configured to contribute to maintaining the engagement between the magnetic member and the non-magnetic member during a given period of time. Following the given period of time, which can correspond to the healing time period, the degradation of the mechanical properties of the retention member can result in the retention member not contributing to maintaining the engagement between the magnetic member and the non-magnetic member, such that the magnetic member and the non-magnetic member can disengage from each other. The disengagement of the magnetic member and the non-magnetic member results in at least two smaller portions of the magnetic implant being no longer engaged together, i.e., that are floating relative to each other, such that excretion, or passing, of each one of the non-magnetic member and the magnetically coupled magnetic members from the patient can be facilitated.

Various implementations and features of the magnetic implant and associated retention member will now be described in greater detail in the following paragraphs.

General Description of the System for Forming an Anastomosis

With reference to FIGS. 1 to 14, a system 10 for forming an anastomosis between two adjacent walls of hollow organs of the digestive tract is shown. Referring more particularly to FIG. 1, in the implementation shown, the system 10 includes a first magnetic implant 12, which can be configured for instance implantation in the stomach; and a second magnetic implant 14, which can be configured for instance for implantation in the jejunum. It is to be understood that the term "implant" in the present description refers to a device that is implanted in the digestive tract for a certain period of time, e.g., the healing time period, before removal from the body, and that the term "implant" can be used interchangeably with the term "device" for instance. In this implementation, the stomach represents a first hollow organ of the digestive tract into which the first magnetic implant 12 can be implanted, and the jejunum represents a second hollow organ into which the second magnetic implant 14 can be implanted, so as to compress a portion of the stomach wall and a portion of the jejunum wall therebetween. The first implant 12 and the second implant 14 can of course be implanted in other portions of the digestive tract of the patient, such as in the duodenum and the ileum, respectively, or any other suitable location to create an anastomosis.

In FIGS. 1-20, each one of the first magnetic implant 12 and the second magnetic implant 14 includes a retention member 16, which is illustrated as a flange 32 provided alongside the periphery of the housing 22 of the magnetic implant. In the implementation shown, each one of the first magnetic implant 12 and the second magnetic implant 14 also includes a connecting member 18 that can be releasably engageable with a connector, such as a delivery catheter. In other words, the magnetic implant 12, 14 can include a feature that enables its connection to a connector for navigating the magnetic implant 12, 14 to a desired site for the anastomosis. In turn, the connecting member 18 can include any feature that enables a releasable connection of the magnetic implant 12, 14 with the connector. In FIGS. 1-20, the connecting member 18 corresponds to a catheter-receiving cavity 74 that includes a catheter attachment assembly (now shown). The catheter-receiving cavity 74 is configured to receive a distal end of the connector, which as mentioned above can be a delivery catheter. In other implementations, the connecting member can include a loop, such as a loop made of a wire, that extends outwardly from a longitudinal end of the magnetic implant to enable grasping by a distal end of a connector, such as a delivery catheter.

In the implementation shown in FIGS. 1-20, each one of the magnetic implants 12, 14 includes a magnetic member 60 and two non-magnetic members 62. More particularly, the magnetic member 60 includes, at each of its longitudinal ends 64, a non-magnetic member engaging portion 67 configured for engaging a corresponding one of the non-magnetic members 62, the magnetic member 60 and the non-magnetic members 62 being components of a magnetic implant 12, 14. The non-magnetic members 62 are thus provided in a longitudinally adjacent relationship relative to the magnetic member 60. It is to be understood that although two non-magnetic members 62 are shown in the illustrated implementation, in other implementations, only one non-magnetic member 62 can be provided in a longitudinally adjacent relationship relative to the magnetic member 60. Furthermore, in other implementations, the non-magnetic member 62 can be provided in a laterally adjacent relationship relative to the magnetic member 60, which can also contribute to create a large anastomosis.

Figure 21A:
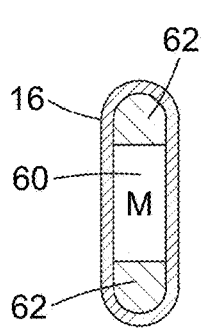
FIG. 21A is a top view of a magnetic implant in accordance with another implementation, the magnetic implant comprising a magnetic member, first and second non-magnetic members, and a retention member.
Figure 21B:
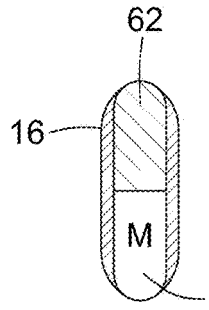
FIG. 21B is a top view of a magnetic implant in accordance with another implementation, the magnetic implant comprising a magnetic member, a non-magnetic member, and a retention member.
Figure 21C:
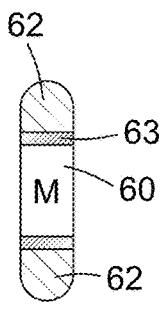
FIG. 21C is a top view of a magnetic implant in accordance with another implementation, the magnetic implant comprising a magnetic member, first and second non-magnetic members, and first and second defeatable portions.
Figure 21D:
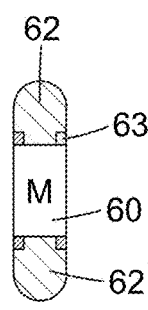
FIG. 21D is a top view of a magnetic implant in accordance with another implementation, the magnetic implant comprising a magnetic member, first and second non-magnetic members, and first and second defeatable portions provided as discrete elements.
Figure 21E:
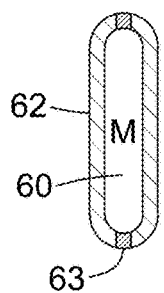
FIG. 21E is a top view of a magnetic implant in accordance with another implementation, the magnetic implant comprising a magnetic member, first and second non-magnetic members provided on each lateral side of the magnetic member, and first and second defeatable portions provided at corresponding longitudinal ends of the magnetic implant.
Figure 21F:
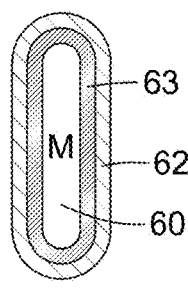
Figure 21G:
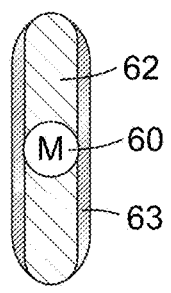
FIG. 21G is a top view of a magnetic implant in accordance with another implementation, the magnetic implant comprising a magnetic member having a substantially circular shape, a non-magnetic member provided in a longitudinally adjacent relationship relative to the magnetic member, and a retention member.
Figures 21H, 21I:
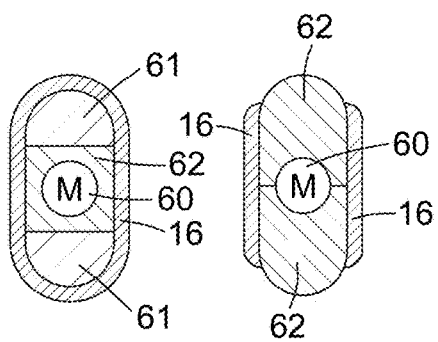
FIG. 21H is a top view of a magnetic implant in accordance with another implementation, the magnetic implant comprising a magnetic member having a substantially circular shape, a non-magnetic member surrounding the magnetic member, an additional non-magnetic member provided at each longitudinal end of the non-magnetic member, and a retention member.
FIG. 21I is a top view of a magnetic implant in accordance with another implementation, the magnetic implant comprising a magnetic member having a substantially circular shape, first and second non-magnetic members joined in a middle region of the magnetic implant, and a retention member.
Figure 21J:
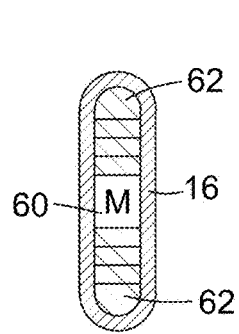
FIG. 21J is a top view of a magnetic implant in accordance with another implementation, the magnetic implant comprising a magnetic member, first, second, third and fourth non-magnetic members provided in a longitudinally adjacent relationship relative to the magnetic member, fifth, sixth, seventh and eighth non-magnetic-members provided in a longitudinally adjacent relationship relative to the magnetic member, and a retention member.
Figure 21K:
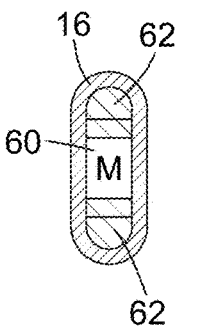
FIG. 21K is a top view of a magnetic implant in accordance with another implementation, the magnetic implant comprising a magnetic member, first and second non-magnetic members provided in a longitudinally adjacent relationship relative to the magnetic member, third and fourth non-magnetic members provided in a longitudinally adjacent relationship relative to the magnetic member, and a retention member.
Figure 21L:
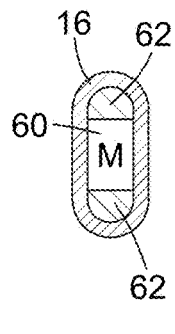
FIG. 21L is a top view of a magnetic implant in accordance with another implementation, the magnetic implant comprising a magnetic member, a non-magnetic members provided in a longitudinally adjacent relationship relative to the magnetic member, and a retention member.
Figures 21M, 21N:
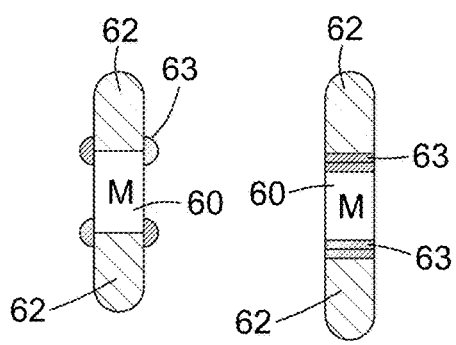
FIG. 21M is a top view of a magnetic implant in accordance with another implementation, the magnetic implant comprising a magnetic member, first and second non-magnetic members and first, second third and fourth defeatable portions each spanning a transition from the magnetic member to one of the non-magnetic member, on a side thereof.
FIG. 21N is a top view of a magnetic implant in accordance with another implementation, the magnetic implant comprising a magnetic member, first and second non-magnetic members, two defeatable portions provided at a transition between the first non-magnetic member and the magnetic member, and two defeatable portions provided at a transition between the second non-magnetic member and the magnetic member.
Figure 21O:
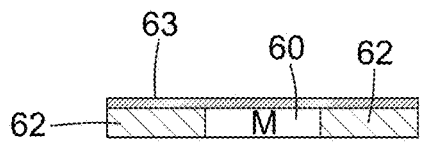
FIG. 21O is a side view of a magnetic implant in accordance with another implementation, the magnetic implant comprising a magnetic member, first and second non-magnetic members, and a defeatable portion provided onto the magnetic member and non-magnetic members.
Figure 21P:
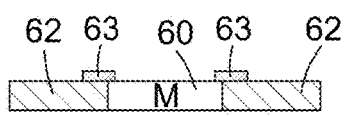
FIG. 21P is a side view of a magnetic implant in accordance with another implementation, the magnetic implant comprising a magnetic member, first and second non-magnetic members and a defeatable portion provided onto the magnetic member and non-magnetic members, at a transition between the first non-magnetic member and the magnetic member and at a transition between the second non-magnetic member and the magnetic member.

FIGS. 21A-21P illustrates example of various configurations that the combination of the magnetic member and the non-magnetic member(s) can have to form the magnetic implant, with or without the presence of a retention member.

For instance, FIG. 21B illustrates an implementation where the magnetic implant includes a magnetic member 60 (or "M") and a single non-magnetic member 62, with a retention member 16 provided around a portion of the outer periphery of the magnetic implant.

FIG. 21C illustrates an implementation where the magnetic implant includes a magnetic member 60, two non-magnetic members 62 and two defeatable portions 63, without a retention member. Each defeatable portion 63 is located between a respective one of the non-magnetic member 62 and the magnetic member 60. FIG. 21D is similar to FIG. 21D, although the defeatable portion 63 includes discrete elements.

FIG. 21E illustrates an implementation where non-magnetic members 62 are provided on each lateral side of the magnetic member 60, with a defeatable portion 63 being provided at each longitudinal end of the non-magnetic members 62 to contribute to initially retain the non-magnetic members 62 and the magnetic member 60 together and then enable separation of the non-magnetic members 62 into two portions over time.

FIG. 21F illustrates an implementation where the non-magnetic member 62 surrounds the magnetic member 60, with the non-magnetic member 62 being made of a material that changes configuration over time, e.g., to reduce its size and eventually separate from the magnetic member 60. A defeatable portion 63 is provided between the magnetic member 60 and the non-magnetic member 62.

FIG. 21G illustrates an implementation where the magnetic member 60 has a substantially circular, or elliptic, shape, with a non-magnetic member 62 being provided in a longitudinally adjacent relationship relative to the magnetic member 60, and a retention member 16 provided around a portion of the outer periphery of the magnetic implant.

FIG. 21H is similar to FIG. 21G, although an additional non-magnetic member 61 is provided at each longitudinal end of the non-magnetic member 62 surrounding the magnetic member 60.

FIG. 21I illustrates an implementation where the magnetic member 60 has a substantially circular, or elliptic, shape, with two non-magnetic members 62 being provided in a longitudinally adjacent relationship relative to the magnetic member 60, with a retention member 16 provided around a portion of the outer periphery of the magnetic implant. In FIG. 21I, the width of the magnetic member 60 is narrower than the width of the non-magnetic members 62, and the two non-magnetic members 62 are joined in a middle region of the magnetic implant.

FIGS. 21J, 21K and 21L illustrate implementations where two (FIG. 21L), four (FIG. 21K) and eight (FIG. 21J) non-magnetic members are provided in a longitudinally adjacent relationship relative to the magnetic member 60. It is to be understood that any of non-magnetic members can be suitable, and that FIGS. 21J, 21K and 21L are provided as examples only.

FIGS. 21O and 21P illustrate implementations of a magnetic implant that includes a magnetic member 60, two non-magnetic members 62 provided in a longitudinally adjacent relationship relative to the magnetic member 60, with a defeatable portion 63 being provided onto the magnetic member 60 and non-magnetic members 62. In such implementations, the defeatable portion 63 is provided at least at the transition between the magnetic member 60 and a given one of the non-magnetic members 62, i.e., spans the transition between the magnetic member 60 and the non-magnetic member 62, to couple the magnetic member 60 with the given one of the non-magnetic members 62 during a period of time, which can correspond to the healing time period. Following the given period of time, the degradation of the defeatable portion 63 can enable subsequent separation of the magnetic member 60 from the magnetic members 62.

FIG. 21M is similar to FIGS. 21O and 21P, with a defeatable portion 63 spanning the transition between the magnetic member 60 and one of the non-magnetic members 62, albeit on a side of the magnetic implant rather than on a top surface thereof.

Several other alternatives for the combination of the magnetic member and the non-magnetic member(s) can also be implemented.

The location of the one or more non-magnetic members 62 depends at least in part on the characteristics of the resulting anastomosis that is desired, more particularly in terms of size and shape, and on the delivery method used for delivering the magnetic implants to the site of the desired anastomosis. For instance, in some implementations, when it is desired to create a large anastomosis, one or more non-magnetic members 62 can be provided in a longitudinally adjacent relationship relative to the magnetic member 60, as shown in FIGS. 1-20, to increase the effective length of the magnetic implant and thus of the resulting anastomosis. The diameter of the resulting anastomosis is governed by the size of the outer periphery of the magnetic implants used to compress the walls of the digestive tract therebetween, as the body over time remodels the shape of the opening resulting from the necrosis of the tissue between the two magnetic implants to a substantially round anastomosis. As such, round anastomoses having increased diameters can be formed by increasing the length, of effective length, of the magnetic implants. Then, the temporary engagement of the non-magnetic members 62 with the magnetic member 60 enables the non-magnetic members 62 to detach from the magnetic member 60 following a given time period, which facilitates excretion of the magnetic implant. In contrast, a magnetic implant that only includes a magnetic member to arrive at a same effective length as a magnetic implant comprising a magnetic member and a non-magnetic member, and thus that does not separate into smaller components once the healing period is completed, can be undesirably difficult to navigate through the digestive tract for excretion. The presence of the non-magnetic members 62 in addition to the magnetic member 60 thus contributes to increasing the effective size of the magnetic implant, and more particularly when the non-magnetic members 62 are provided in a longitudinally adjacent relationship relative to the magnetic member 60, the effective length of the magnetic implant.

The engagement of the magnetic member 60 and the non-magnetic members 62 during the healing time period can be maintained at least in part given the presence of the retention member 16 that extends outwardly from the magnetic implant at least on either side of the location of the engagement between the magnetic member 60 and the non-magnetic members 62, as shown in the figures. In other words, the retention member 16 is provided such that it can limit the longitudinal translation, or traveling, of either one of the magnetic member 60 or the non-magnetic member 62 such that the magnetic member 60 and the non-magnetic member 62 remain in position during the healing time period. The retention member 16 can thus have a dual role of maintaining the magnetic implant in position to prevent premature passage of the magnetic implant through the necrotic area during the healing time period, and maintaining the engagement of the magnetic member and the non-magnetic member during the healing time period to increase the effective length of the magnetic implant and facilitate excretion, or passing, of the components of the magnetic implant once the healing time period is completed and the magnetic member and the non-magnetic member are no longer engaged together.

In some implementations and as shown in FIGS. 1-20, the magnetic member 60 of the magnetic implant 12, 14 can include a housing 22 that encloses at least one magnet 24 therein. The housing 22 can include for instance an outward portion 26 and an inward portion 28. The inward portion 28 of the housing 22 includes the portion of the housing that faces the corresponding other magnetic implant and is involved in the magnetic compression of the tissue, while the outward portion 28 of the housing 22 is on the opposed side of the magnetic implant facing away from the tissue being compressed. In this example, the two housing components 26, 28 surround the magnet and can be coupled together around a periphery thereof. In some implementations, the housing 22 can be made of a single piece that fully encloses the magnet 24 therein, as shown for instance in FIG. 14. Other housing constructions are also possible, where one or more housing components are used to partly or fully enclose the magnet 24. The housing 22 can include various features to facilitate engagement with the retention member 16 and the non-magnetic member 62, as will be discussed in further detail below.

Each of these components of the system for forming an anastomosis, i.e., the magnetic member, the non-magnetic member, and the retention member, will now be described in further detail.

Description of the Magnetic Implant

Still referring to FIGS. 1-14, the first magnetic implant 12 is a device that is implantable into a first hollow organ of the digestive tract of a patient at a site of a desired anastomosis via the lumen of the first hollow organ. Examples of hollow organs of the digestive tract include the oesophagus, stomach, duodenum, jejunum, ileum, colon, biliary tract, and pancreatic duct. A site of desired anastomosis can be determined according to the condition of the patient, and this aspect will not be discussed further in the context of the present description. As used herein, the expression "magnetic implant" refers to a structure that can be implanted into the chosen hollow organ of the digestive tract, and that can be magnetically attracted to another magnetic implant due to magnetic forces. In some implementations, the magnetic implant can consist of a magnet. In some implementations, the magnetic implant can include a magnet and one or more additional features, such as a housing and/or a connecting member. The two magnetic implants can be substantially the same as each other, or different, in terms of their shape, configuration, construction, and/or material make-up. These features will be further discussed below.

The first magnetic implant 12 is used with a second magnetic implant 14 to form a magnetic implant pair. The second magnetic implant 14 is a device implantable into a second hollow organ of the digestive tract of the patient to the site of the desired anastomosis via the lumen of the second hollow organ. The second hollow organ of the digestive tract is located in sufficiently close proximity of the first hollow organ to enable the convergence of the respective wall tissue of the first hollow organ and the second hollow organ to eventually form the anastomosis.

The first and second magnetic implants 12, 14 are configured to remain within the digestive tract for at least a given healing time period. The healing time period enables necrosis of the anastomosis area while providing enough time for the edge of scar tissue to form. In some implementations, after approximately 3 to 5 days following implantation of the pair of magnetic implants at the desired site of the anastomosis, the periphery of the anastomosis is strengthened by collagen deposition, with the formation of an edge of scar tissue having an increased tensile strength occurring at an estimated of approximately 7 to 10 days following implantation. The duration for forming the scar tissue can vary depending on the overall health of the individual patient, and depending on the specific parts of the digestive tract being joined. The scar tissue can also gain strength over the course of several additional weeks. In some implementations, it may be desirable for the magnetic implants to be released and passed out of the body of the patient about two weeks after implantation. In some implementations, the healing time period can thus be at least about 3 days, at least about one week, at least about two weeks, or between about 2 weeks to about 4 weeks.

Each one of the first and second magnetic implants 12 can be navigated to the site of the desired anastomosis using various techniques. For instance, the magnetic implants 12, 14 can be delivered to the site of the desired anastomosis endoscopically or laparoscopically. Examples of techniques for delivering at least one of the magnetic implants 12, 14 laparoscopically are described for instance in U.S. application Ser. No. 17/524,502, which is hereby incorporated by reference in its entirety.

Each one of the first and second magnetic implants 12, 14 can have any suitable shape and size determined in accordance with their intended purpose. In some implementations, the size and the shape of the magnetic implant can be determined for instance in accordance with the characteristics of the site of the desired anastomosis, the delivery technique chosen to deliver the magnetic implant to the site of the desired anastomosis, and so on. In some implementations, the magnetic implant can have for example an elliptic shape, a circular shape, an elongated shape, a rectangular shape, an octagonal shape, or any other polygonal shape in terms of its cross-section. The magnetic implant can include rounded corners to facilitate navigation into the digestive tract.

The magnetic implant can have an aspect ratio of about 1:1 (e.g., in the case of a circular cross-section), or any aspect ratio above 1:1. In the context of the present description, the expression "aspect ratio" is intended to refer to a length to width ratio. In some implementations, the magnetic implant can have an aspect ratio of about 1.1:1 to about 40:1, about 1.5:1 to about 20:1, about 1.5:1 to about 15:1, about 1.5:1 to about 4:1, about 2:1 to about 6:1, about 4:1 to about 15:1, for example, or can have another aspect ratio. Although the examples illustrated in FIGS. 1-21 are shown to have an elongated shape, it is to be understood that any one of the configurations exemplified in FIGS. 1-21 can also be adapted to have an aspect ratio closer to or of about 1:1 and up.

The choice of the aspect ratio of the magnetic implant can depend on the hollow organ into which the magnetic implant is intended to be implanted, e.g., on whether it is desired to create an anastomosis between two bowel segments (bowel-bowel anastomosis) or between the stomach and a bowel segment (stomach-bowel anastomosis). In some implementations, a large gastro-bowel anastomosis can initially be created to subsequently yield an anastomosis of a desired size, smaller than the initial large gastro-bowel anastomosis. In other words, when a healed gastro-bowel anastomosis is desired to have a given size, the initial gastro-bowel anastomosis can have a larger size than the desired size of the healed gastro-bowel anastomosis, since the remodeling of the initial gastro-bowel anastomosis can reduce its size over time. The larger size of the initial gastro-bowel anastomosis can involve using a magnetic implant having a larger length to width ratio than the desired size of the healed gastro-bowel anastomosis, since the length to width ratio of the magnetic implant drives the size of the initial anastomosis. Over time, the initial gastro-bowel anastomosis will remodel to a smaller size to arrive at the desired size of the healed gastro-bowel anastomosis. In the case of a bowel-bowel anastomosis, the reduction in size between the initial bowel-bowel anastomosis and the healed bowel-bowel anastomosis can be less pronounced than in the case of a stomach-bowel anastomosis, and the length to width ratio of the magnetic implant can be closer to the desired size of the healed bowel-bowel anastomosis.

In some implementations, when creating an anastomosis between two small bowel segments, for instance, between the duodenum and the ileum, the aspect ratio can be more than 1:1 and less than 4:1, or the aspect ratio can range from about 2:1 to about 4:1, from about 1.5:1 to about 3:1, or from about 2:1 to about 3:1, to name a few examples. It has been found that an aspect ratio of more than 1:1 and less than 4:1 can have benefits when creating an anastomosis between two small bowel segments, for instance between the duodenum and ileum, such as providing an appropriate size of magnetic implants for delivery at the desired site of the anastomosis while achieving an operational anastomosis at that location. In some implementations, when creating an anastomosis between the stomach and a small bowel segment, for instance, between the stomach and the jejunum, the aspect ratio can range from about 2:1 to about 40:1, or from about 3:1 to about 15:1, to name a few examples.

It is also to be understood that although the aspect ratio of more than 1:1 and less than 4:1 has been presented above in relation with a magnetic implant comprising a magnetic member and one or more non-magnetic members, a magnetic implant that does not include a non-magnetic member and that is intended for implantation in the duodenum or the ileum for creating a bowel-bowel anastomosis can also have an aspect ratio of more than 1:1 and less than 4:1, or an aspect ratio between 1:1 and 15:1.

In some implementations, the shape and size of the retention member 16 can be adapted in accordance with the shape and size of the corresponding magnetic implant. For instance, in some implementations, the height of the magnetic implant can be proportional to the thickness of the magnet contained therein and hence be chosen to be proportional to the desired magnetic strength of the resulting magnetic implant. Furthermore, the size of the magnetic member 60 relative to the non-magnetic member 62 can also vary. For instance, in some implementations, the magnetic member 60 can be sized so as to have a magnetic member length that represents more than about 50%, more than about 60%, or more than about 70% of the effective length of the magnetic implant, i.e., the overall length of the magnetic implant. In some implementations, the magnetic member 60 can be sized so as to have a magnetic member length that represents between about 40% to about 70% of the effective length of the magnetic implant.

Each of the first and second magnetic implants 12, 14 includes a compression surface 30 that is configured to contact the tissue of the corresponding hollow organ. The compression surface 30 can also be referred to as a tissue-contacting surface, since it is the surface of the magnetic implant that is eventually in contact with the interior wall of the hollow organ once the magnetic implant is delivered to the site of the desired anastomosis. Each of the first and second magnetic implants 12, 14 also includes a lumen-oriented surface opposite the tissue-contacting surface, the lumen-oriented surface generally facing the lumen of the hollow organ once the magnetic implant is delivered to the site of the desired anastomosis. It is to be understood that the compression surface 30 includes the tissue-contacting portion of both the magnetic member 60 and the non-magnetic member 62, or non-magnetic members if more than one is present.

In some implementations, the compression surface 30 can be substantially continuous and flat, as shown in FIGS. 1-20. This can contribute to evenly distribute the force of the magnetic implant onto the tissue once the first and second magnetic implants 12, 14 are magnetically coupled together. In other implementations, the compression surface 30 of the first magnetic implant 12 can have a complementary shape compared to the compression surface 30 of the second magnetic implant 14. For instance, the first magnetic implant 12 can have a curvilinear surface that is outwardly curved, i.e., convex, and the second magnetic implant 14 can have a complimentary curvilinear surface that is inwardly curved, i.e., concave, for the first magnetic implant 12 to mate therewith.

The compression surface 30 can include features such as ridges, crests, furrows, grooves, and the like, to provide a surface roughness to the compression surface 30. In the implementation shown in FIGS. 1-13, the surface roughness of the compression surface 30 is provided by the series of furrows distributed in a grid pattern over the compression surface 30. In some implementations, the compression surface 30 of the first magnetic implant 12 can include a series of ridges, and the second magnetic implant 14 can include a complimentary series of furrows such that when the first and second magnetic implants 12, 14 are magnetically coupled, the first and second magnetic implants 12, 14 can interlock and/or self-align to increase the stability of their positioning on their respective sides of the first and second hollow organs. In some implementations, the surface roughness of the compression surface 30 can also facilitate adherence of the wall tissue against which the magnetic implant is placed, which can eventually contribute to maintain the non-magnetic members at the desired site of the anastomosis during the healing time period. Once the healing time period is completed, the non-magnetic member can also remain adhered to a portion the wall tissue for a certain period of time, without impairing the subsequent excretion, or passing, of the non-magnetic member.

In some implementations, the magnetic member 60 of the magnetic implant can include one or more magnets 24 received within the housing 22. The magnet 24 can be any type of suitable magnet composed of the appropriate material. In some implementations, the magnet 24 can be chosen according to its attractive force, i.e., according to the pressure that will be exerted on the surface area of the tissue that will eventually be compressed between the first and second magnetic implants 12, 14. Factors influencing the attractive force of the magnet 24 can include the shape of the magnet 24, the thickness of the magnet 24, the material of which the magnet 24 is made, etc. Example materials include neodymium magnets (e.g., NdFeB magnets), rare earth magnets, and ferrite magnets.

In some implementations, the magnet or magnets of the magnetic member of a first magnetic implant may be made of a magnetic material that is not permanently magnetized, such as soft magnetic alloys, e.g., nickel-iron, silicon iron, iron, iron-cobalt, and ferritic stainless steels. In other words, the magnet(s) of the magnetic member of respective magnetic implants may not be constructed of two permanent magnets. In other implementations, the magnet(s) of the corresponding magnetic member of a first and second magnetic implants may be constructed of two permanent magnets.

Housing

In some implementations, the magnetic member 60 of the magnetic implant 12, 14 can include a housing 22 configured to house the magnet 24 therein. An example of housing 22 is shown in FIGS. 1-20. More particularly with reference to FIG. 2, the housing 22 is shown as including an outward portion 26 and an inward portion 28. In the context of the present description, the terms "outward" and "inward" when referring to the housing 22 are used in accordance with a radial reference system, in which the wall of the hollow organ is considered to be outwardly positioned relative to the lumen of the hollow organ. When the housing 22 is present, the outward portion 26 of the housing 22 is the portion that includes the lumen-oriented surface of the magnetic member 60, and the inward portion 28 of the housing 22 is the portion that includes the tissue-contacting surface or the compression surface 30 of the magnetic member 60. In the implementation shown, the outward portion 26 and the inward portion 28 together fully enclose a single magnet therein. In other implementations, the single magnet can be fully enclosed in a single-piece housing, i.e., a housing that is made of a single unit, the single unit including the tissue-contacting surface and the lumen-oriented surface, in accordance with the description above and as shown in FIG. 14 for instance. In other words, instead of comprising two halves as shown in FIGS. 1-13, the housing 22 of the magnetic member 60 can be made of a single piece that fully encloses the magnet 24 therein.

In some implementations, the magnetic member 60 can include a housing that is configured to receive multiple magnets therein. Providing multiple magnets within a single housing can contribute to enhancing the flexibility of the magnetic implant, such that it can become easier to bend when subjected to a force. Alternatively, the multiple magnets can each be received in a corresponding housing, and the multiple magnets can be connected to each other by various means. In implementations where each magnet is received in a corresponding housing, the multiple magnets can be flexibly connected to each other.

In some implementations, when each magnetic member includes a single magnet, the single magnet can facilitate alignment of the magnetic implants on either side of the walls of the digestive tract to enable magnetic coupling of the magnetic implants. For example, when using a single magnet having a length of 2 inches compared to a magnet that includes four magnets having a length of 0.5 inches each, the alignment between the two single magnets is more likely to be accurate compared to the equivalent length obtained by the four magnets. The use of a single magnet for the magnetic member can enable the magnetic implants to self-align or self-locate, reducing the risk of misalignment that can be observed when multiple magnets are used.

The description made above regarding the characteristics of the compression surface of the magnetic implant is applicable to the housing 22 when the housing is present or when housings are present.

The housing 22 of the magnetic member 60 can include a plurality of strut-engaging openings 66 that are sized and configured to receive therein a corresponding strut 68 of the retention member 16, the struts 68 extending inwardly from the flange 32, toward the magnetic implant. The housing 22 can also include a runner-receiving portion 72 sized and configured to enable abutment of the runner 70 of the retention member 16 thereon. It is to be understood that the configuration of the housing 22 can depend on the configuration of the retention member 16, such that the housing 22 and the retention member 16 can interact with each other to contribute to the engagement of the magnetic member 60 with the non-magnetic member 62 and limit the longitudinal motion of the magnetic member 60 and the non-magnetic member 62 relative to each other during the healing time period. In order to achieve these goals, in the implementation shown in FIGS. 1-13, the strut-engaging openings 66 defined in the housing 22 are sized such that a corresponding strut 68 fits therein in a substantially "flush" manner to limit the longitudinal motion of the magnetic member 60 and the non-magnetic member 62 relative to each other during the healing time period. The struts 68 are thus trapped in the strut-engaging openings 66 to provide interference to the longitudinal translation of the retention member 16 relative to the magnetic member 60 and the non-magnetic members 62.

Non-Magnetic Member

The non-magnetic member 62 is a component of the magnetic implant that is non-magnetic, and as such, does not include a magnet for the purpose of creating a compression anastomosis. The non-magnetic property of the non-magnetic member 62 enables preventing the non-magnetic member 62 from magnetically coupling with the magnetic members 60 following disengagement of the non-magnetic member 62 from the magnetic member 60 after the healing time period. In other words, given that one of the objectives of the multi-component magnetic implant is that the magnetic implant divides itself into its individual components once the healing period is completed to facilitate excretion, the non-magnetic feature of the non-magnetic member 62 prevents the non-magnetic member 62 from magnetically coupling with the magnetic members to avoid a disorganized or undesirable magnetic attraction that could result in a larger combination of components having to be excreted or the formation of an anastomosis at an undesired location. It is to be noted that the magnetic members 60 of each one of the first and second magnetic implants 12, 14 will remain magnetically attracted to each other following the healing time period and will likely be excreted as a combined unit composed of the two magnetic members.

The non-magnetic member 62 can have various configurations. For instance, in the implementation shown in FIGS. 1-13, the non-magnetic member 62 includes two halves that are joined together once engaged with the magnetic member 60. Providing the non-magnetic member 62 as a two-piece non-magnetic member can contribute to facilitate excretion of the non-magnetic member as smaller pieces. In other implementations, the non-magnetic member 62 can be a single piece component, as shown in FIG. 14. The non-magnetic member can be "full", or solid, as shown in FIGS. 2, 3, 9 and 10. Alternatively, the non-magnetic member can include a void, i.e., can be a hollow structure.

The non-magnetic member 60 can include a feature having the functionality of a retention member. For instance, in the figures, the non-magnetic member 60 includes a non-magnetic member flange 71 at a distal portion thereof. The non-magnetic member flange 71 can be configured as a portion of the retention member 16 so as to provide a continuously-shaped retention member 16 around the magnetic implant once the non-magnetic member 62 and the magnetic member 60 are engaged together. A continuously-shaped retention member 16 comprising the non-magnetic member flange 71 is shown for instance in the top view of the magnetic implant 14 illustrated in FIG. 5. In such implementations, the retention member 16 thus includes the flange 71 of the non-magnetic member 62 and the flange 32, with the flange 71 being integral with the remaining of the non-magnetic member 62.

As mentioned above, each one of the first magnetic implant 12 and the second magnetic implant 14 includes a connecting member 18 that can be releasably engageable with a connector such as a delivery catheter or a laparoscopic device. In the implementation shown, the connecting member 18 is defined in the non-magnetic member 62, in a distal portion thereof. The connecting member 18 can include any feature that enables a releasable connection of the magnetic implant 12, 14, and more particularly the non-magnetic member when the magnetic member 60 and the non-magnetic member 62 are provided in a longitudinally adjacent relationship, with the connector. In some implementations, the connecting member 18 can correspond to a catheter-receiving cavity 74 that includes a catheter attachment assembly (now shown). The catheter-receiving cavity 74 is configured to receive a distal end of the connector, which can be a delivery catheter or a laparoscopic device, for instance.

Figure 10:
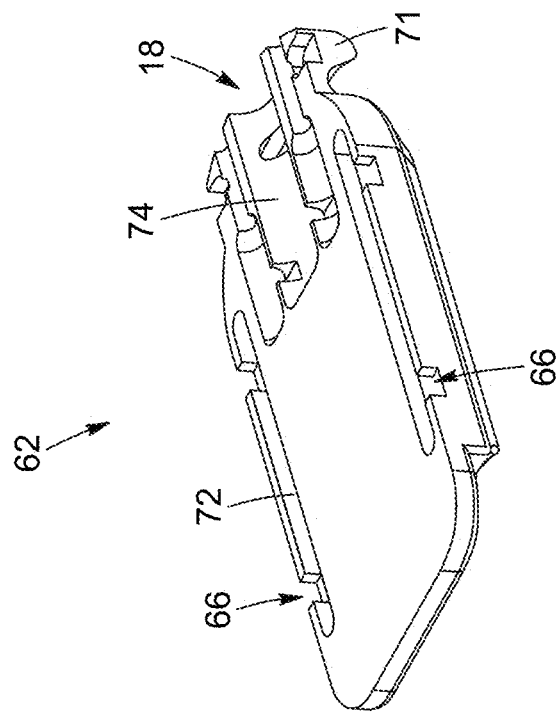
FIG. 10 is a perspective view of the half of the non-magnetic member of the second magnetic implant shown in FIG. 9.
Figure 9:
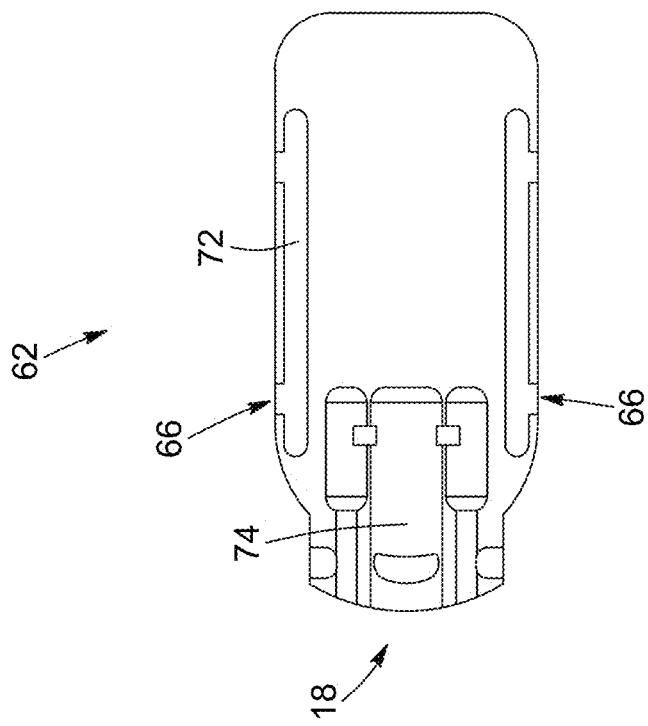
FIG. 9 is a top view of a half of the first non-magnetic member of the second magnetic implant shown in FIG. 2.
Figure 11:
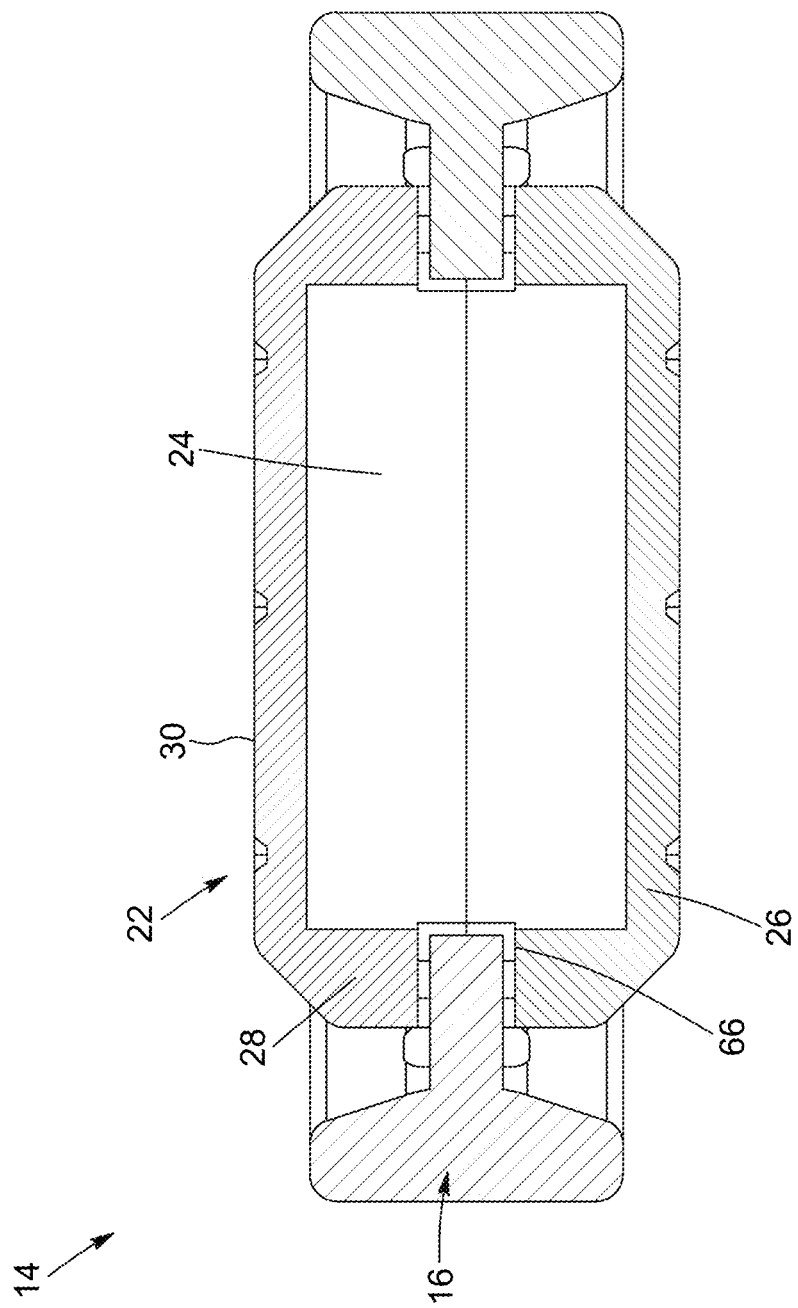
FIG. 11 is a cross-sectional view of the second magnetic implant, showing two halves of the housing and a magnet contained therein, and the retention member.
Figure 12:
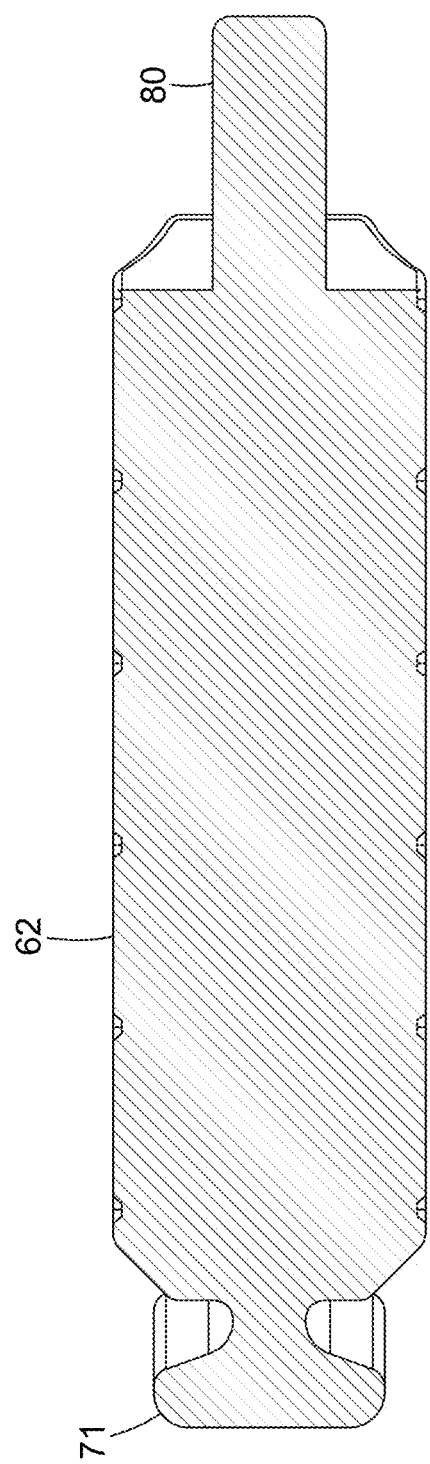
FIG. 12 is a cross-sectional view of the second non-magnetic member of the second magnetic implant shown in FIG. 1, with the two halves of the first non-magnetic member shown coupled to each other.

Similarly to the magnetic member 60, the non-magnetic member 62 also includes a plurality of strut-engaging openings 66 that are sized and configured to receive therein a corresponding strut 68 of the retention member 16, the struts 68 extending inwardly from the flange 32 toward the magnetic implant (as shown for instance in FIGS. 9 and 10). The non-magnetic member 62 also includes a runner-receiving portion 72 sized and configured to enable abutment of the runner 70 of the retention member 16 thereon. In the implementation shown, the runner-receiving portion 72 is shaped as a groove into which the runner 70 of the retention member 16 can be received and abutted to stabilize the retention member 16 and minimize the longitudinal motion of the magnetic member 60 relative to the non-magnetic member 62.

Interaction Between the Magnetic Member and the Non-Magnetic Member

Figure 13:
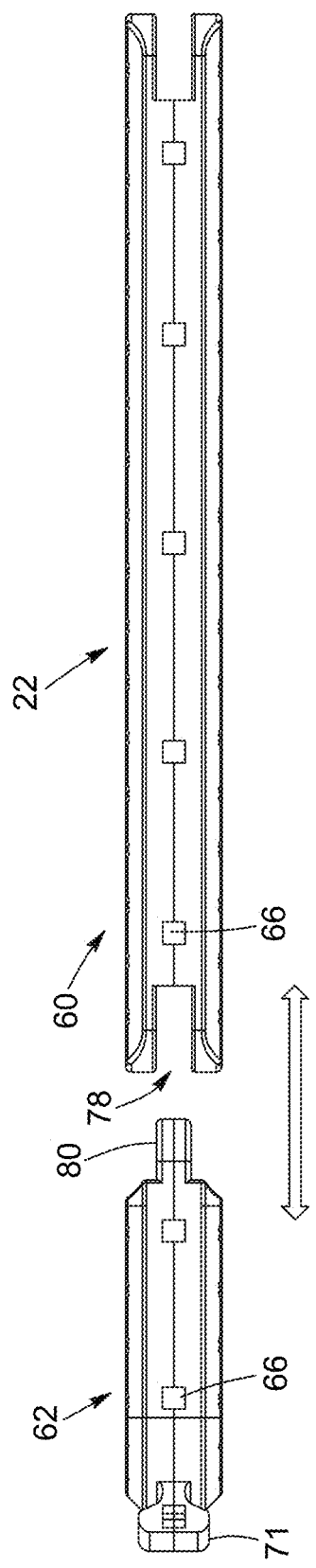
FIG. 13 is a side view of the second non-magnetic member and magnetic member of the second magnetic implant shown in FIG. 1, the first non-magnetic member and the magnetic member being engaged together via a male-female engagement.
Figure 14A:
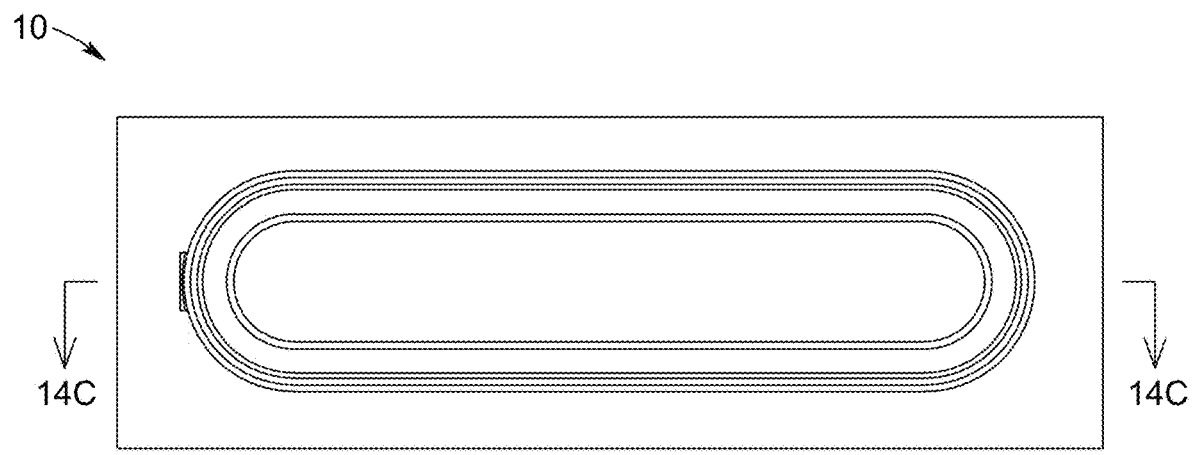
FIG. 14A is a top view of first and second magnetic implants in accordance with another implementation.
Figure 14B:
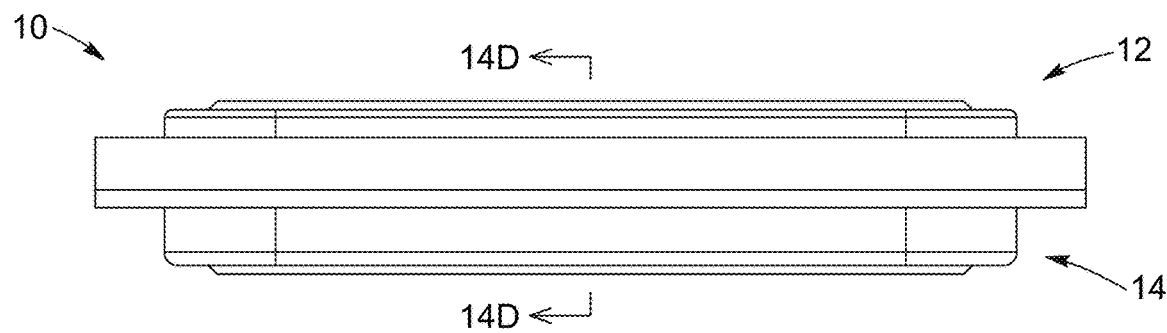
Figure 14C:
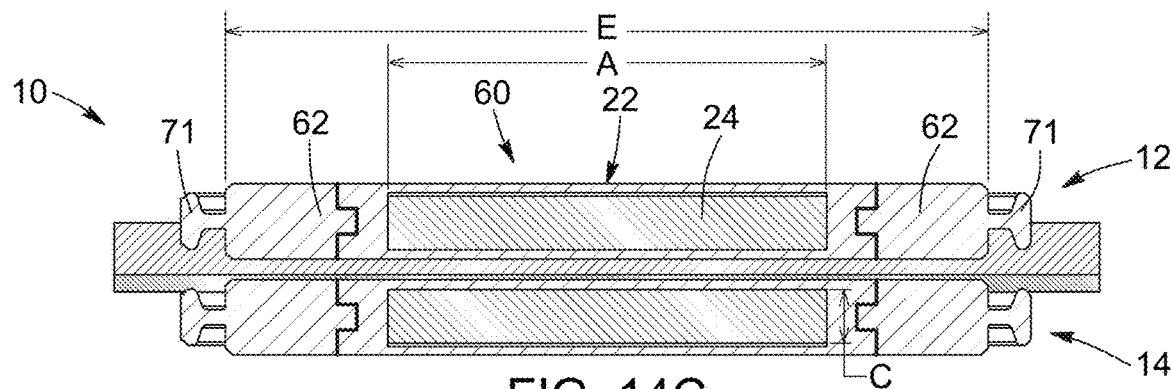
FIG. 14C is a cross-sectional view of the first and second magnetic implants shown in FIG. 14a, each magnetic implant comprising a magnetic member, first and second non-magnetic members, and a retention member.
Figure 14D:
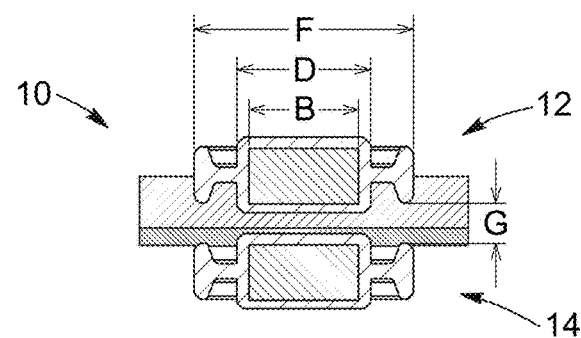
FIG. 14D is a cross-sectional view of the first and second magnetic implants of FIG. 14b.

The magnetic member 60 and the non-magnetic member 62 can be engaged together via various types of engagements. In the implementation shown in FIGS. 1-14, the magnetic member 60 and the non-magnetic members 62 are engaged together via a male-female interaction. Referring more particularly to FIG. 13, the housing 22 of the magnetic member 60 can include a non-magnetic member receiving cavity 78 that is sized and configured for receiving a non-magnetic member projection 80 of the non-magnetic member 62 therein. The size of the non-magnetic member projection 80, and more particularly its length, can be chosen so as to minimize the up and down movement of the non-magnetic member 62 relative to the magnetic member 60, along the lateral axis of the magnetic implant. Such an interaction between the magnetic member 60 and the non-magnetic member 62 can enable transfer of the bending load from the magnetic member 60 to the non-magnetic member 62, so that the non-magnetic member 62 can contribute to the application of pressure onto the wall of the digestive tract once the magnetic members 60 on either side of the two adjacent walls of the digestive tract are magnetically coupled to each other. In other words, the non-magnetic member projection 80 can be configured to be long enough so that, during the healing time period, the rotational movement of the non-magnetic member 62 about an axis extending transversally across the non-magnetic member projection 80 is minimized, such that at least part of the bending load resulting from the magnetic coupling of the two magnetic members 60 is transferred to the non-magnetic member 62. The presence of the retention member 16 maintaining the magnetic member 60 and the non-magnetic member 62 in an engaged configuration during the healing time period also contributes to the distribution of the bending load along both the magnetic member 60 and the non-magnetic member 62 to increase the effective length of the magnetic implant. Once the healing time period is completed and the retention member 16 starts to lose its physical integrity and no longer contributes to maintaining the magnetic member 60 and the non-magnetic member 62 in an engaged configuration, the natural movement in the digestive tract will facilitate disengagement of the magnetic member 60 and the non-magnetic member 62, initially via a outward translation of the non-magnetic member 62 relative to the magnetic member 60, such that the magnetic member 60 and the non-magnetic member 62 become free from each other.

It is to be understood that although the implementation shown in FIGS. 1-14 illustrates the housing 22 of the magnetic member 60 having a non-magnetic member receiving cavity 78 for receiving a non-magnetic member projection 80 therein, the reverse configuration is also possible. In such scenarios, the non-magnetic member includes a magnetic member receiving cavity sized and configured for receiving a magnetic member projection therein.

In other implementations, the temporary engagement between the magnetic member and the non-magnetic member can be achieved via other means than a male-female interaction.

An example of another type of engagement between a magnetic member and a non-magnetic member of a magnetic implant is exemplified in FIGS. 15-20. In the implementation shown, the magnetic implant 12 includes a magnetic member 60 and a non-magnetic member 62 provided in a longitudinal adjacent relationship relative to the magnetic member 60, i.e., one non-magnetic member 62 being provided at each longitudinal end 64 of the magnetic member 60. In this implementation, the retention member 16 forms an integral part of the housing 22 and the non-magnetic members 62. It is to be understood that although a retention member 16 is shown in FIGS. 15-20, the retention member 16 can also be omitted.

In the implementation shown in FIGS. 15-20, the transition between the housing 22 encasing the magnet 24 and the non-magnetic members 62 includes a defeatable portion 63 that is configured to modify its configuration or structure once the healing time period is completed or has sufficiently progressed, or at a given timepoint during or after the healing time period. The defeatable portion 63 can be defeatable for instance via a mechanical and/or chemical mechanisms, e.g., dissolution, degradation, breakage of target parts of the retention member, etc. The characteristics of the defeatable portion 63 can enable the non-magnetic member 62 and the magnetic member 60 to initially be retained together via any type of connection, coupling or engagement, and then, can enable the non-magnetic members 62 to detach, or separate, from the magnetic member 60 once the healing time period is completed, to enable excretion of smaller components compared to the original magnetic implants. In some implementations, the defeatable portion 63 can include a plurality of struts, or can include regions having a reduced thickness and/or a reduced width, for instance, which can facilitate the disintegration of the defeatable portion to enable the magnetic member 60 and the non-magnetic member 62 to separate from each other. The defeatable portion 63 can also be a continuity of the non-magnetic member and/or the housing, and be made of a material that degrades at a faster rate compared to the magnetic member and the non-magnetic member, as will be discussed in further detail below.

Figure 15:
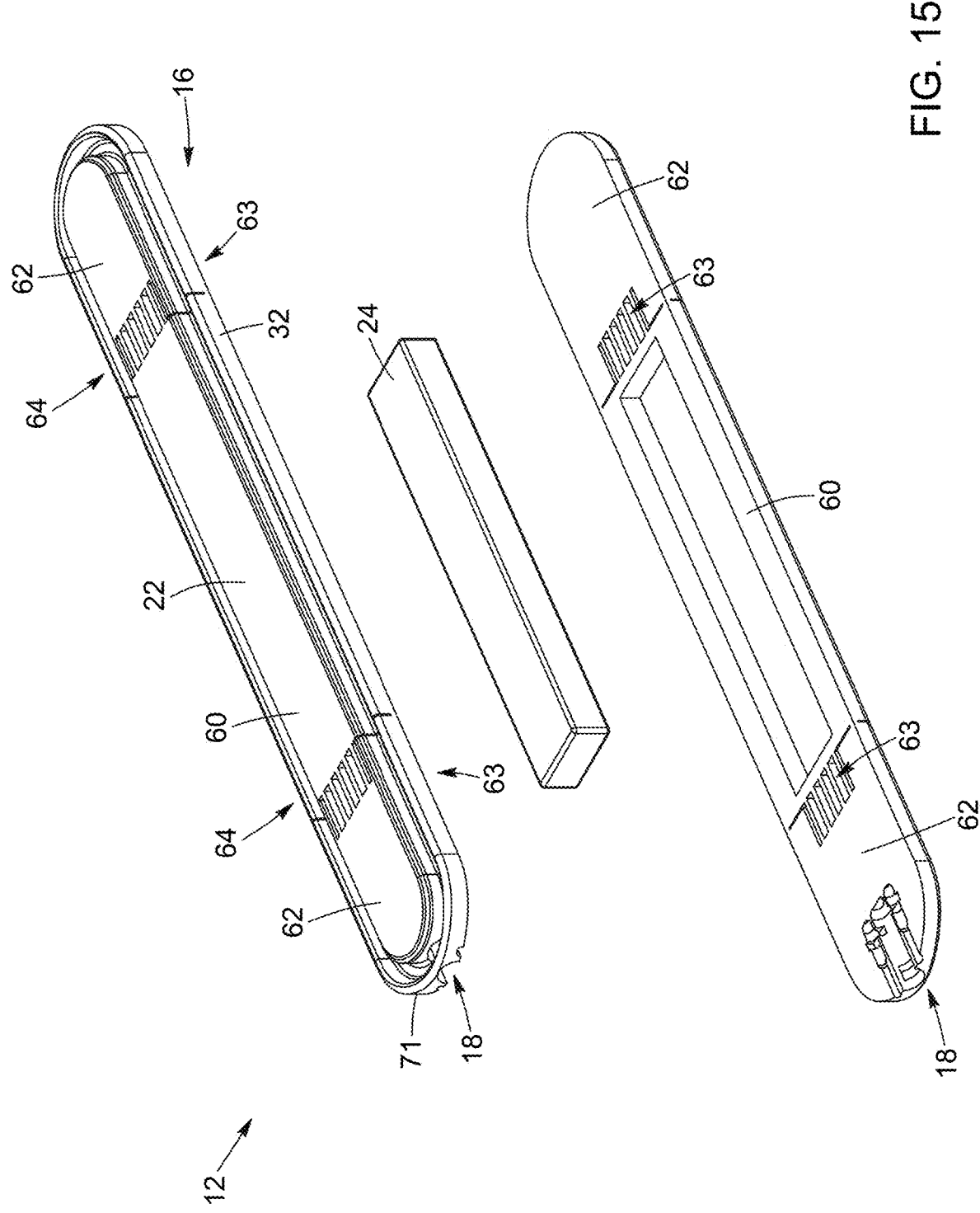
FIG. 15 is an exploded perspective view of a magnetic implant in accordance with another implementation, the magnetic implant comprising a magnetic member, first and second non-magnetic members and first and second defeatable portions, the first defeatable portion being provided between the first non-magnetic member and the magnetic member and the second defeatable portion being provided between the second non-magnetic member and the magnetic member.
Figure 16:
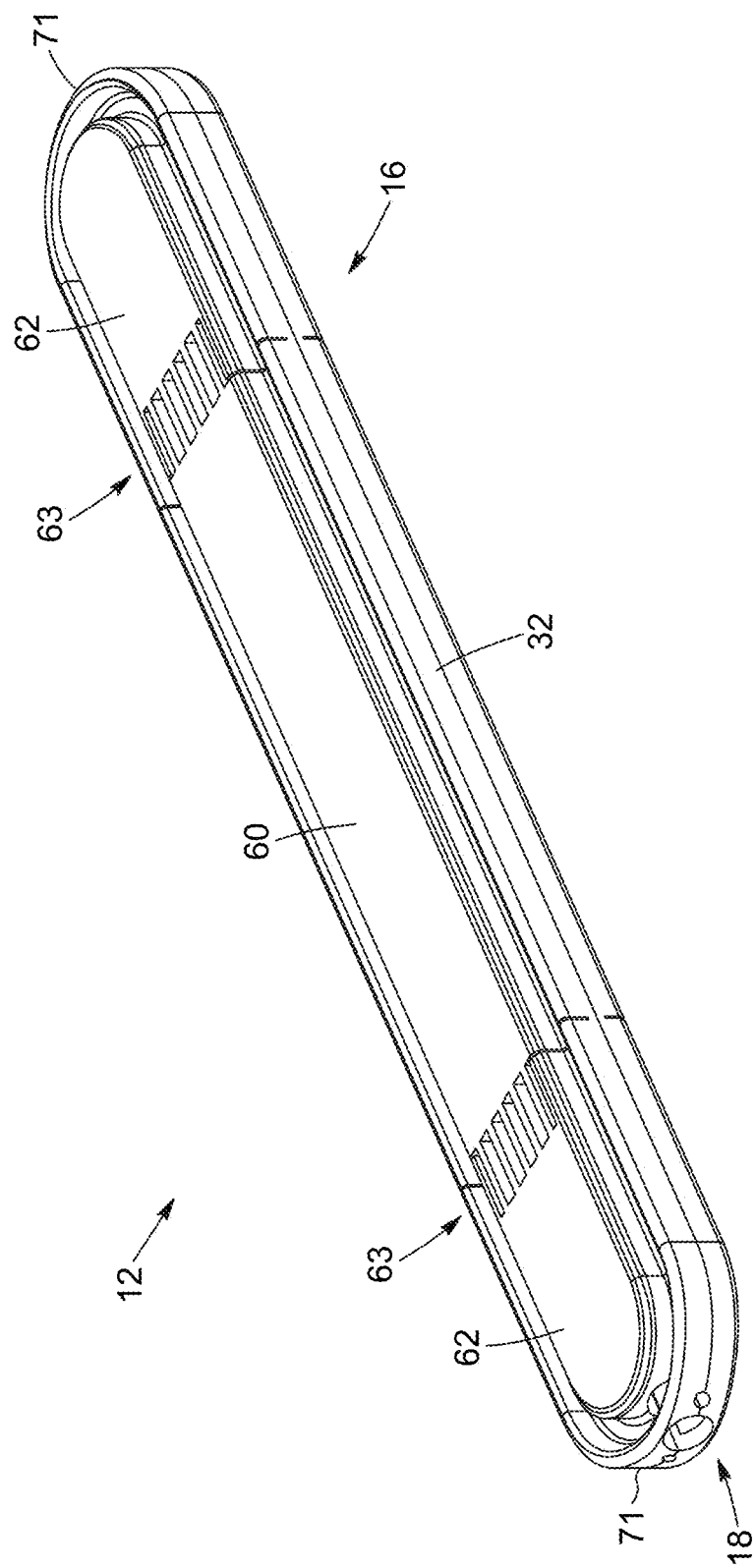
FIG. 16 is a perspective view of the magnetic implant of FIG. 15.

In such implementations, components forming half of the housing 22 and half of the non-magnetic members 62, which would correspond to one half of the magnetic implant without the magnet 24 itself as shown in FIG. 15, can be manufactured as a single piece. Alternatively, the non-magnetic members 62 and a first half of the housing 22 can be manufactured as a single piece, with the second half of the housing 22 being coupled to the first half of the housing 22 once the magnet 24 has been placed inside. In yet other implementations, any component of the magnetic implant shown in FIGS. 15-20 can be manufactured as a single component, and be glued together, i.e., joined by an adhesive, with the other components to obtain the magnetic implant, be snaped fitted, be polymer welded, or the components can be joined by any other suitable means. In this implementation, the retention member 16 is configured as an integral part of the housing 22 and the non-magnetic member 60. Thus, in this implementation, the retention member 16 can change configuration during the healing time period, although the change in configuration of the defeatable portion 63 can have a more significant impact on the engagement and disengagement of the magnetic member 60 with the non-magnetic members 62 and subsequent separation thereof.

Figure 18:
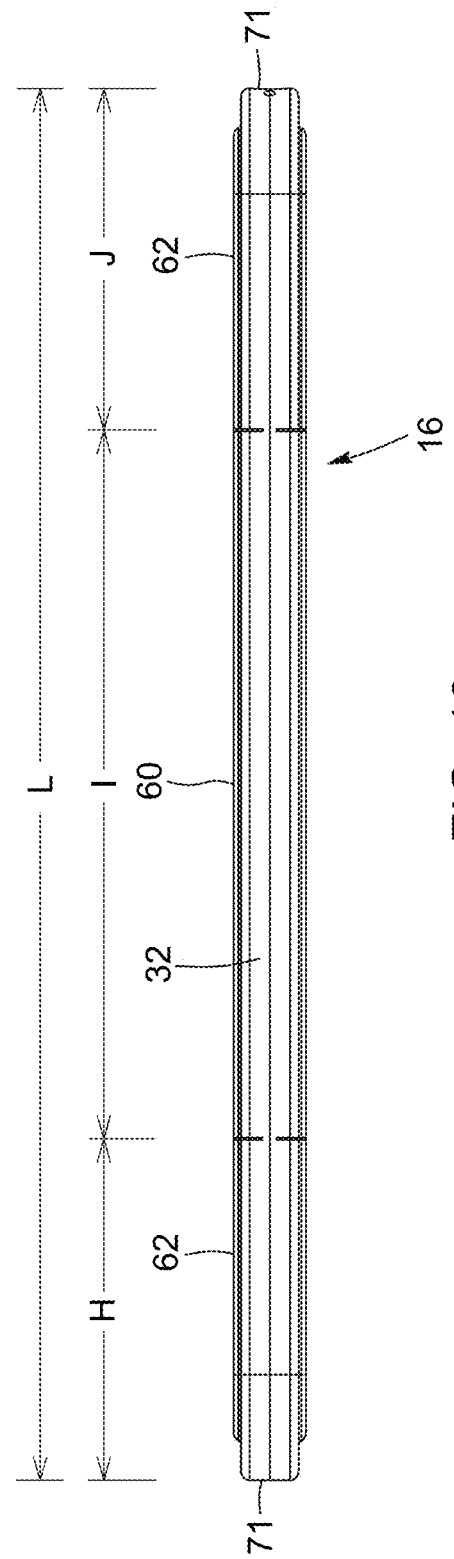
FIG. 18 is a side view of the magnetic implant of FIG. 15.
Figure 19:
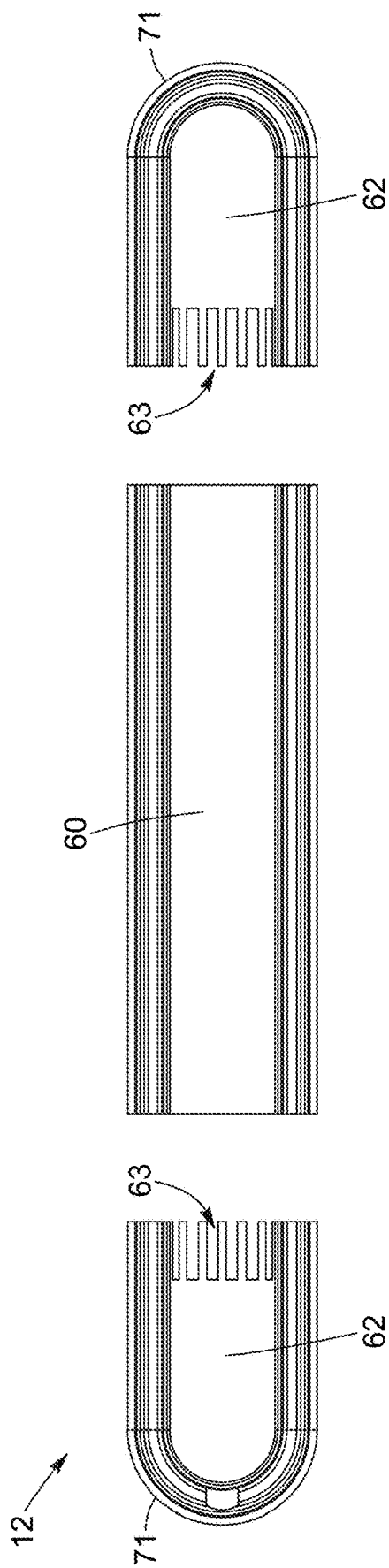
FIG. 19 is an exploded top view of the magnetic implant of FIG. 15, shown after a healing time period.
Figure 20:
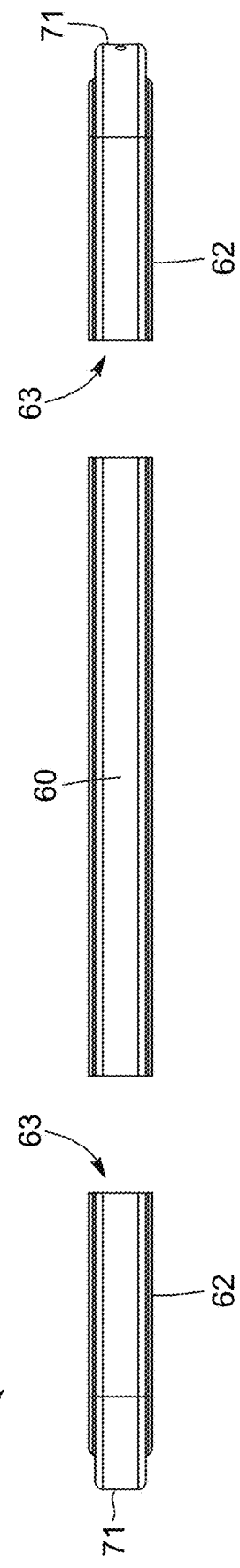
FIG. 20 is an exploded top view of the magnetic implant of FIG. 19.

In the implementation shown in FIGS. 19 and 20, the magnetic member 60 is shown following degradation of the housing 22 initially present around the magnet 24, when a portion of the housing 22 is made of a defeatable material such as a bioresorbable material. In such implementations, the housing 22 can include a plurality of successive layers, each layer having given characteristics. For instance, the outermost layer can be made of a defeatable material as described above, and the layer underneath can be made of a material that is generally not defeatable under the conditions of implantation of the magnetic implant in the digestive tract, such as polyether ether ketone (PEEK), polycarbonate, Ultem™, polyphenylsulfone (PPSU), or a 3D printable biocompatible resin. The underneath layer can be useful for instance to properly enclose the magnet and maintain the integrity of the magnet once the outermost layer of the housing 22 has degraded over time. Alternatively, both the outermost layer and the underneath layer can be made of a defeatable material Description of the Retention Member Still referring to FIGS. 1-20 and as mentioned above, the system 10 for forming an anastomosis between two adjacent walls of hollow organs of the digestive tract includes a retention member 16 that extends, or projects, outwardly from a corresponding one of the first and second magnetic implants 12, 14, e.g., from a peripheral wall of the corresponding one of the first and second magnetic implants 12, 14. Reference to an outward extension when describing the retention member 16 is also made in accordance with a radial reference system, with an outward extension meaning an extension or projection away from the compression surface 30 of the magnetic implant 12, 14.

The retention member 16 can be any structure that enables the retention of the pair of the magnetic implants 12, 14 in position once magnetically coupled and during the healing time period, to prevent the first and second magnetic implants 12, 14 to prematurely pass through the necrotic area, and that enables maintaining the engagement between the magnetic member 60 and the non-magnetic member 62 during the healing time period while enabling disengagement of the magnetic member 60 and the non-magnetic member 62 following the healing time period. The retention member 16 thus temporarily retains the magnetic and non-magnetic components together.

In the implementation shown in FIGS. 1-13, the retention member 16 includes a flange 32, a runner 70, and a plurality of struts 68, the runner 70 and the plurality of struts 68 contributing to maintaining the engagement of the magnetic member 60 with the non-magnetic member 62 during the healing time period.

The retention member 16 is configured to have a modifiable configuration as the healing time period progresses. Various strategies can be implemented to provide a retention member 16 having a modifiable configuration as the healing time period progresses. For instance, the retention member 16 can be made of a bioresorbable material that is configured to at least partially disintegrate and/or resorb during the healing time period such that once the healing time period is completed, the interference provided by the retention member 16 to maintain the connection, or engagement, between the magnetic member 60 and the non-magnetic member 62, and to maintain the pair of magnetic implants 12, 14 in place at the anastomosis site, is no longer sufficient. At this point in time, the magnetic member 60 and the non-magnetic member 62 become disengaged, and the non-magnetic member 62 or the components of the non-magnetic member 62 can be excreted as single components, and the pair of magnetic members 60 that are still magnetically coupled to each other can also be passed through the anastomosis site and be excreted as smaller components compared to the original overall magnetic implants 12, 14 that include both the magnetic member 60 and the non-magnetic member 62.

In some implementations, the retention member 16 can also include features that facilitate the breaking apart of the retention member 16 once the healing time period is completed. For instance, the retention member 16 can be configured to be defeatable once the healing time period is completed. In the context of the present description, the term "defeatable" refers to the capacity of the retention member 16 to modify its configuration or structure once the healing time period is completed or has sufficiently progressed, or at a given timepoint during or after the healing time period. The retention member 16 can be defeatable for instance via a mechanical and/or chemical mechanisms, e.g., dissolution, degradation, breakage of target parts of the retention member, etc. When the retention member 16 is defeatable via chemical mechanisms, it is meant that the retention member 16 can be made of a material, such as a resorbable material, that is subjected to dissolution or degradation in the environment in which the magnetic implant is implanted. In addition to the resorbable material from which can be made the retention member 16, the retention member 16 can include one or more portions that promote the breaking apart of the retention member 16 from the remainder of the magnetic implant to further contribute to the dissolution, degradation, and/or fragmentation of the retention member 16. The breaking apart of the retention member 16 can be facilitated for instance by the presence of a different material, such as a resorbable material, or by a given configuration of the retention member 16. For instance, in the implementation shown in FIGS. 1-14, the presence of the struts 68 can facilitate the mechanical defeatability of the retention member 16 from the corresponding magnetic implant.

In some implementations, the retention member 16 can be configured so as to be chronically loaded. The chronic load can be intrinsic to the manufacturing process or the assembly of the components of the magnetic implant, or can be a result of loading when the magnetic implants are magnetically coupled together with tissue of the digestive tract compressed in between. For instance, in the implementations shown in FIGS. 1-20, the retention member 16 can be chronically loaded by the tissue trapped between the magnetic implants 12, 14 during the healing time period and in turn, the chronic loading applies a bending and shear force on the struts 68 and runner 70. As the material degrades in size and mechanical integrity during and/or after the healing time period, the chronic load can accelerate failure of the material from which is manufactured the struts 68 and runner 70. In some implementations, the time to failure can be determined according to the geometry and loading of the retention member 16. In addition, when the retention member 16 is manufactured using an additive manufacturing technique such as a fused deposition modeling (FDM) technique, the layer lines can be extruded in an anisotropic manner such that the loading forces relative to the direction of extrudate can contribute to accelerate the mechanical degradation or failure of the retention member 16.

The retention member 16 can thus include a defeatable portion that is breakable or disintegrable into smaller pieces once the healing time period is completed, the size of which will depend on the degree of advancement of the chemical degradation of the material from which is made the retention member 16 or the defeatable portions thereof. The material from which is made the retention member 16, or at least some portions of the retention member 16, can thus be one that, when subjected to a particular set of conditions, changes configuration or make-up. In the case of a retention member 16 that is defeatable, the change in configuration is one that at least enables disengagement between the magnetic member 60 and the non-magnetic member 62. The set of conditions can include a duration, which can correspond to the healing time period, the pH surrounding the retention member 16, and the temperature surrounding the retention member 16. For instance, it can be determined that a material known to dissolve or disintegrate after about two weeks, at a strong acidic pH and at temperatures of about 37° C., would be suitable to be used for the retention member 16 on a device intended to be implanted in the stomach.

Figure 2:
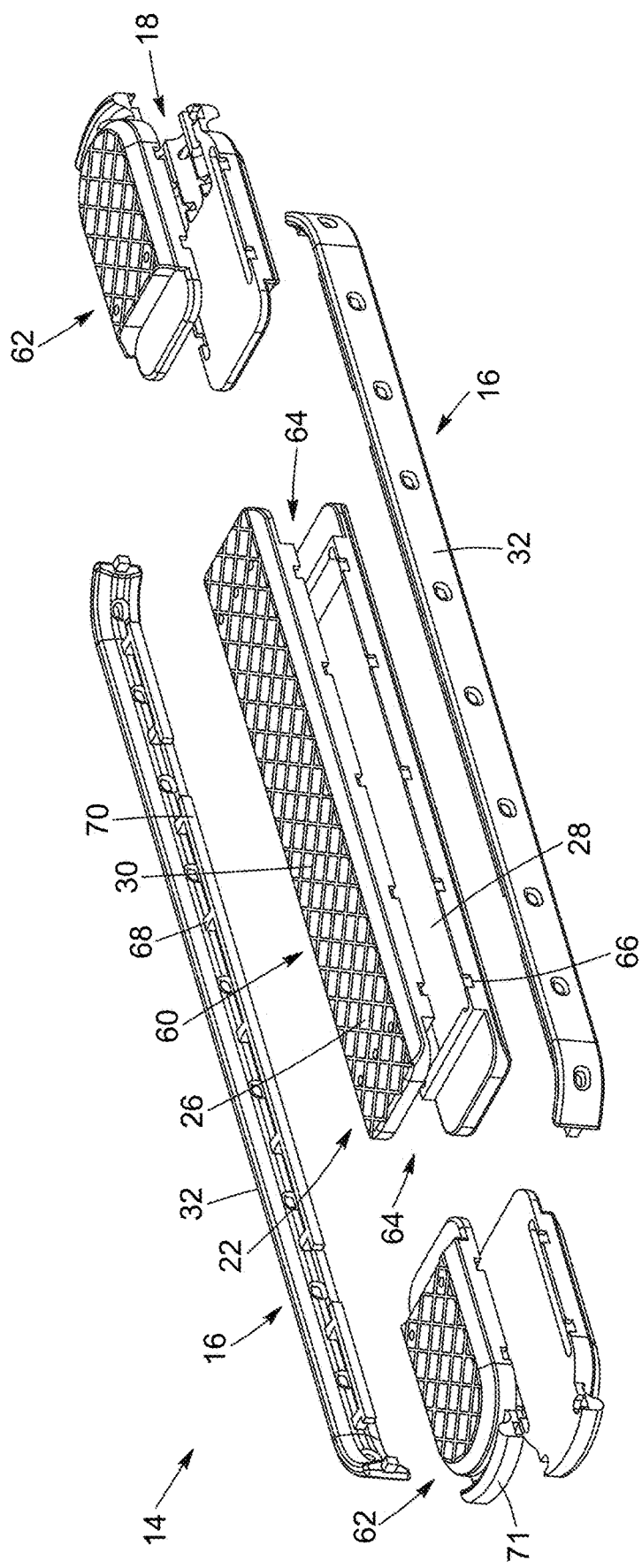
FIG. 2 is an exploded perspective view of the second magnetic implant of FIG. 1.
Figure 3:
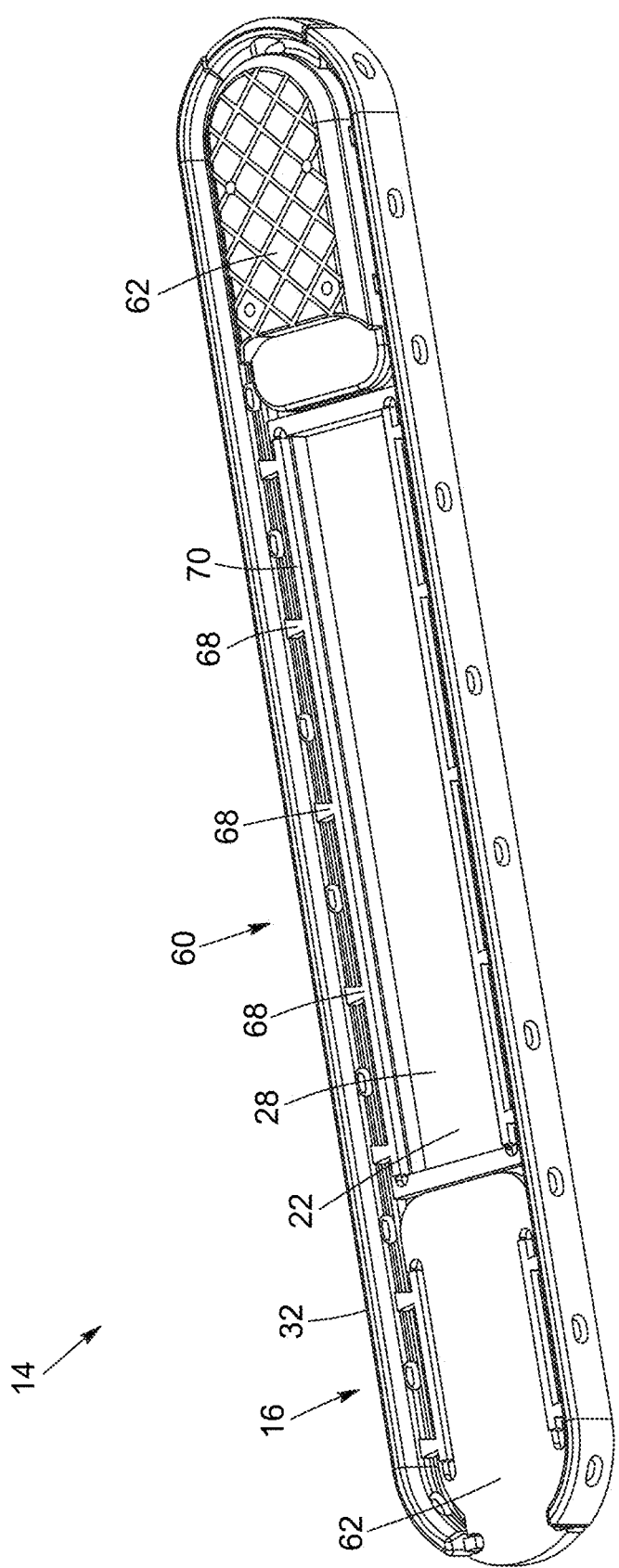
FIG. 3 is a perspective view of components of the second magnetic implant of FIG. 1, showing a half of the second non-magnetic member at a first longitudinal end, two halves of the first non-magnetic member at a second longitudinal end, a half of a housing provided between the first and second non-magnetic members, and the retention member.
Figure 4:
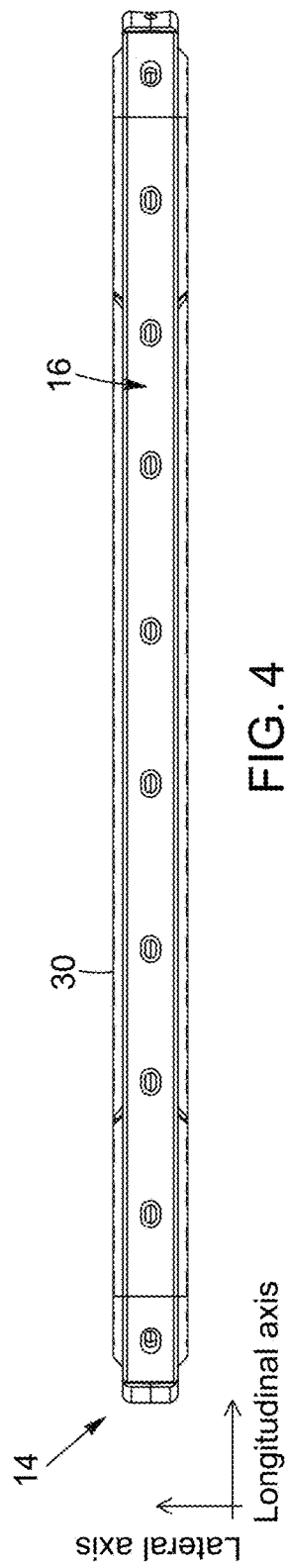
FIG. 4 is a side view of the second magnetic implant of FIG. 1, along a longitudinal axis thereof.

In some implementations and with reference more particularly to FIGS. 2 and 3, the retention member 16 can include a flange 32 that extends continuously around substantially the entire periphery, i.e., peripheral wall, of the corresponding magnetic implant, and thus the entire periphery of the magnetic member 60 and the non-magnetic member 62. The flange 32 may extend around all but a small portion of the periphery, with minimally overlapping, i.e., spanning or bridging, the transition between the magnetic member 60 and the non-magnetic member 62. In other implementations, the retention member 16 can include a series of flange extensions that are provided in a spaced-apart relationship around the periphery of the corresponding magnetic implant, with still at least one flange extension being provided on either side of the magnetic implant to minimally overlapping or bridging the transition between the magnetic member 60 and the non-magnetic member 62. Thus, when a series of flange extensions is provided as the retention member 16, the flange extensions are disposed as discrete flanges located at given locations, i.e., extending radially, around the periphery of the corresponding magnetic implant and in a number such that the retention member 16 can retain the pair of magnetic implants at the desired site of the anastomosis once implanted in the digestive tract of the patient and magnetically coupled. The positioning of the flange extensions can depend on whether one or two non-magnetic members 62 are provided in a longitudinal relationship relative to the magnetic member 60. An example of a configuration of a series of flange extensions when the magnetic implant includes a magnetic member 60 and a non-magnetic member 62 provided on both sides of the magnetic member 60 can include a flange extension overlapping each transition between the magnetic member 60 and the non-magnetic member 62 on both sides of the magnetic implant, and optionally a flange extension being provided at each distal end of the magnetic implant, i.e., at each longitudinal end of the non-magnetic members 62, which would correspond to the non-magnetic member flanges 71.

The location and number of the flanges of a series of flanges can also be determined at least in part by the characteristics of the tissue against which the magnetic implant will rest, the desired stability of the magnetic implant once implanted in the digestive tract, the material of which is made the flanges, and the mechanism by which the flanges can eventually defeat, among others. The size of the flanges, when provided as a series of discrete flanges, can also vary according to various factors.

In some implementations, the retention members 16 of a pair of magnetic implants 12, 14 can be configured to maintain a gap G between the inner surface of a first retention member of a first magnetic implant and the inner surface of a second retention member of a second magnetic implant once implanted in the digestive tract. In some implementations, the gap G can be such that a space remains between the inner surface of the retention member 16 and the surface of the vessel against which the compression surface 30 of the magnetic implant rests once the magnetic implants are magnetically coupled to each other in the digestive tract. In other implementations, the gap G can be such that the inner surface of the retention member contacts or gently presses the surface of the vessel, such as shown in FIG. 14. FIG. 14 illustrates a pair of magnetic implants 12, 14 being magnetically coupled to each other through the vessel wall of the stomach, shown in dark pink, and the vessel wall of the jejunum, shown in pale pink. The retention member 16 is shown as having a T-shaped configuration when viewed as a cross-section, as also shown in FIGS. 1-13. It is to be understood that the retention member 16 can have a different shape than the T-shape shown in the Figures. For instance, the retention member can have any configuration as described in U.S. application Ser. No. 17/477,790, which is incorporated herein by reference in its entirety.

Figure 17:
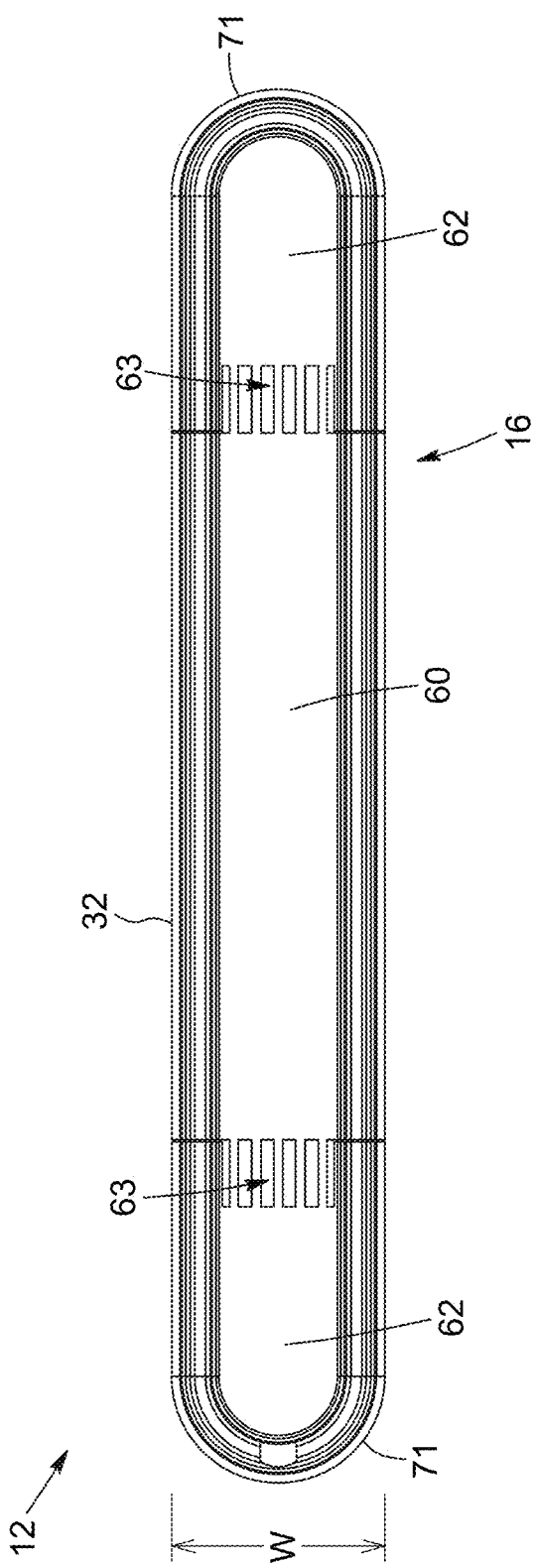
FIG. 17 is a top view of the magnetic implant of FIG. 15.

Examples of approximate dimensions, in millimeters, that the magnetic implants can have in certain scenarios are provided in Table 1 below, with reference letters A to G being as illustrated in FIG. 14, for Table 1, and with reference letters H, I, J, L and Was being illustrated in FIGS. 17 and 18, for Table 2.

TABLE 1

|  | A | B | C | D | E | F | G |
|---|---|---|---|---|---|---|---|
| Example #1 | 25.4 | 6.35 | 3.175 | 7.747 | 44.196 | 7.75 | 2.3 |
| Example #2 | 25.4 | 6.35 | 3.175 | 7.747 | 44.196 | 12.7 | 2.3 |
| Example #3 | 25.4 | 6.35 | 3.175 | 7.747 | 44.196 | 16.5 | 2.3 |

TABLE 2

|  | H | I | J | L | W |
|---|---|---|---|---|---|
| Example #4 | 10 | 55 | 10 | 75 | 10 |
| Example #5 | 15 | 40 | 15 | 70 | 15 |
| Example #6 | 30 | 65 | 30 | 125 | 20 |
| Example #7 | 5 | 20 | 5 | 30 | 10 |
| Example #8 | 10 | 35 | 10 | 55 | 15 |

It is to be understood that the non-limitative examples presented above are for illustrative purposes only, as the magnetic implants can have various dimensions. For instance, in some implementations, the overall length of the magnetic implant can vary from about 25 mm to about 120 mm. In some implementations, the magnetic member can have a length ranging from about 15 mm to about 70 mm. In some implementations, the non-magnetic members, when two are present and provided in a longitudinally adjacent relationship relative to the magnetic member or when a single non-magnetic member is provided, can each have a length ranging from about 5 mm to about 35 mm. In some implementations, the magnetic implant can have a width ranging from about 4 mm to about 15 mm. The width of the magnetic implant can depend on the diameter of the vessel or organ into which it is implanted. In some implementations, the width of the magnetic implant can be such that the magnetic implant fits within the working channel of an endoscope. In some implementations, the magnetic member of a magnetic implant configured for delivery to the stomach or the jejunum to create a gastro-jejunal anastomosis can have a length ranging from about 35 mm to about 65 mm. In some implementations, the non-magnetic members of a magnetic implant configured for implantation in the stomach or in the jejunum, when two are present and provided in a longitudinally adjacent relationship relative to the magnetic member or when a single non-magnetic member is provided, can each have a length ranging from about 10 mm to about 25 mm. In some implementations, the magnetic member of a magnetic implant configured for implantation in the duodenum or in the ileum can have a length ranging from about 20 mm to about 35 mm. In some implementations, the non-magnetic members of a magnetic implant configured for implantation in the duodenum or in the ileum, when two are present and provided in a longitudinally adjacent relationship relative to the magnetic member or when a single non-magnetic member is provided, can each have a length ranging from about 5 mm to about 15 mm.

In some implementations, the retention member 16 can be configured to provide additional reinforcement to the magnetic implant 12, 14 during the healing time period, and the retention member 16 can be configured such that it applies a pressure that may be sufficient to cause necrosis but at a slower rate than the necrosis occurring between the compression surfaces 30 of the magnetic implants 12, 14 once they are magnetically coupled.

In other implementations, the retention member 16 can be configured to engage the periphery of the anastomosis at a pressure interference amount that does not result in necrosis of the tissue that is in contact with the retention member 16. In such implementations, the retention member "footprint" is larger than the desired anastomosis, and the interference resulting from the presence of the retention member 16 can discourage the magnetic implants 12, 14 from passing though the anastomosis during the healing time period. Thus, the size and flexibility of the retention member 16 can be such that the magnetic coupling of the magnetic implants 12, 14 can occur even in presence of the retention member 16.

The retention member 16 can thus be configured to provide enough time for the scar edge to form during the healing time period, additional reinforcement or strength to keep the magnetic implants 12, 14 from decoupling or the tissue from perforating or tearing due to loads on the anastomosis site and connected bowel and stomach tissues, and enables maintaining the engagement between the magnetic member 60 and the non-magnetic member 62 during the healing time period. Examples of external or internal loads can include the weight of the bowel or stomach moving due to patient movement and/or internal loads from peristalsis, bowel spasm/constriction, and internal gas pressure changes.

In some implementations, the retention member 16 can be configured to provide additional mechanical support to prevent premature separation of the magnetic implants 12, 14, and tissue stretching/tearing or leak due to physiologic loads that can result for instance from the weight of the bowel segments and the forces imparted by patient movement, spasm/constriction of the vessels, internal gas pressure changes, etc., on the healing anastomosis site and connected vessels.

In some implementations, the retention member 16 can be configured is so as to not impart enough compression to cause necrosis but to provide an additional surface area to distribute the physiologic loads during healing. As such, the retention member 16 can be configured to be in intimate contact with the surface of the vessel wall once the compression surfaces 30 are magnetically coupled and has compressed the tissues.

In some implementations, the shape, size, and/or configuration of the first magnetic implant 12 can be similar to the configuration of the second magnetic implant 14. In other implementations, the shape, size, and/or configuration of the first magnetic implant 12 can be different from the configuration of the second magnetic implant 14. The choice of whether to use a pair of magnetic implants that include similar or different magnetic implants can depend for instance of the hollow organ into which the respective magnetic implants will be implanted. Whether or not the magnetic implants 12, 14 are similar, the retention member 16 of the respective magnetic implant can also be similar or different, in terms of size, shape, and/or configuration. Once again, the respective hollow organs into which the magnetic implants will eventually be implanted can be a factor in determining whether the corresponding retention member could be similar or different.

Materials

Details regarding different materials that the retention member 16, the non-magnetic member 62, and the housing 22, if present, can be made of will now be provided.

Retention Member and Defeatable Portion

As mentioned above, the retention member and the defeatable portion, depending on which one forms part of the magnetic implant, can be made of or include a material that enables the retention member or the defeatable portion to change configuration over time. Such material can include for instance a bioerodible material, a biodegradable material, and/or a bioresorbable material. A bioerodible material, such as a bioerodible hydrogel, refers to a material, such as a polymer, that exhibits a controlled degradation in a given environment such as under physiological conditions, for instance by undergoing surface erosion. A biodegradable material refers to a material that is susceptible to breakdown, decomposition or degradation under the action of biological processes, such as by enzymatic action. A bioresorbable material refers to a material that can be resorbed or dissolved naturally under physiological conditions. As mentioned above when describing a scenario where the retention member can be defeatable and when describing the defeatable portion, a retention member or a defeatable portion that is made of or that includes one or more portions that are made of a bioerodible material, a biodegradable material, or a bioresorbable material, provides the retention member or the defeatable portion with an initial shape and initial dimensions that enable the retention member or the defeatable portion to maintain the engagement between the magnetic member and the non-magnetic member. Then, over time, the dimensions of the retention member or the defeatable portion are eventually reduced sufficiently to enable disengagement of the magnetic member and the non-magnetic member, such that individual components of the non-magnetic members can be excreted naturally, and the magnetically coupled magnetic members can pass through the necrotic area to also be evacuated either naturally or with the support of an external means.

The choice of material can depend on various factors such as the degradation rate of the material in the environment where the magnetic implant will be implanted, and the stiffness that it provides, which can be chosen to be sufficient for maintaining the structural properties of the magnetic implant during the healing time period. In other words, the material can be chosen so as to provide sufficient stiffness to maintain the engagement of the magnetic member with the non-magnetic member during the healing time period and limit the longitudinal traveling of the magnetic member and the non-magnetic member, and also such that the bending load can be evenly distributed across the surface area of the magnetic implant.

For instance, in some implementations, the retention member or the defeatable portion can be made of an aliphatic polyester or a combination of aliphatic polyesters, or can include one or more portions made of an aliphatic polyester or a combination of aliphatic polyesters. The aliphatic polyester can be a synthetic aliphatic polyester. Examples of aliphatic polyester include polylactic acid, polyglycolic acid, polylactic-co-glycolic acid, polycaprolactone, and polydioxanone.

In some implementations, the retention member or the defeatable portion can be made of a combination of polyhydroxyacetic ester, lactide copolymers and glycolic/lactide copolymers (PLGA).

In some implementations, the retention member or the defeatable portion can be made of at least two materials, each of the materials having a different dissolution rate or a different degradation rate once implanted in a given environment, and in this case, in the respective hollow organ into which is implanted the magnetic implant. The difference in dissolution rate or degradation rate between the at least two materials can result in certain pre-determined portions of the retention member or the defeatable portion to weaken, which in turn can promote the defeatability of the retention member or the defeatable portion. The pre-determined portions of the retention member or the defeatable portion can be for instance notches or thin spots provided at strategic locations.

In some implementations, the dissolution and/or degradation occurring at these strategic locations can be dependent on the pH of the environment where it is implanted. For instance, one or more pre-determined portions of the retention member or the defeatable portion can be subjected to an accelerated dissolution and/or degradation in a strongly acidic environment compared to a weakly acidic environment. Alternatively, one or more pre-determined portions of the retention member or the defeatable portion can be subjected to an accelerated dissolution and/or degradation in a basic environment compared to an acidic environment, for instance when the magnetic implant is intended to be in contact with pancreatic juice, bile and/or pancreatic enzymes. Other considerations that can influence the degradation of the one or more pre-determined portions of the retention member or the defeatable portion can include the presence of bacteria with or without lytic enzymes, and possible drugs interactions such as with H2-receptor blockers or proton pump inhibitors. When the retention member or the defeatable portion is made as a composite of at least two materials, the materials can be selected to provide different properties (e.g., structure, flexibility, degradation, etc.) and the materials can be distributed in various ways in the structure of the retention member or the defeatable portion (e.g., at target locations, evenly distributed throughout, etc.) depending on the overall design of the device.

In some implementations, the retention member 16 or the defeatable portion 63 of both the first magnetic implant 12 and the second magnetic implant 14 can be made of the same material. This scenario can be implemented for instance when the physiological environment of the corresponding two hollow organs of the digestive tract is similar. A similar physiological environment can refer for example to the approximately neutral pH within two segments of the small intestine.

In other implementations, given the property of bioerodible materials, biodegradable materials, or bioresorbable materials to erode, dissolve or degrade at a given rate depending on the environment, a first material can be chosen for the retention member 16 or the defeatable portion 63 of the first magnetic implant 12 for implantation in a given hollow organ, and a second material, different from the first material, can be chosen for the retention member 16 or the defeatable portion 63 of the second magnetic implant 14 for implantation in a different given hollow organ. The retention member or the defeatable portion of the first magnetic implant 12 and the retention member 16 or the defeatable portion 63 of the second magnetic implant 14 can then dissolve or degrade based on the differences in the physiological environment in the respective hollow organs over the healing time period. For example, when the first magnetic implant 12 is intended to be implanted in the stomach, where the pH is strongly acidic, and the second magnetic implant 14 is intended to be implanted in the jejunum, where the pH is weakly acidic, the material of the retention member 16 or the defeatable portion 63 of the first magnetic implant 12 can be different from the material of the retention member 16 or the defeatable portion 63 of the second magnetic implant 63 so as to obtain a similar dissolution rate or degradation rate between the two retention members 16 or the defeatable portions 63. In other words, the design of each retention member 16 or of the defeatable portion 63 can be based on the properties of the hollow organ and corresponding tissue wall (including the tissue thickness, tissue surface characteristics, internal pH and conditions of the hollow organ, and/or other physiological properties) such that the retention members 16 or the defeatable portions 63 of the first and second magnetic implants 12, 14 are defeated after approximately the same time interval.

Non-Magnetic Member

The non-magnetic member 62 can be made of a material that is generally not susceptible to dissolution or degradation, and that would be considered a durable material once implanted in the hollow organ. Examples of such materials can be polymers such as silicones, e.g., polydimethylsiloxane; or a fluoropolymer, e.g., polytetrafluoroethylene. Other examples can include a titanium alloy, cobalt chromium, or an austenitic stainless steel. Other examples can also include any other suitable biocompatible material that retains its integrity for a duration longer than the healing time period.

Alternatively, the non-magnetic member 62 can be made of a material that is susceptible to dissolution or degradation, such as a defeatable material that includes a bioresorbable material, that is the same or different as the material from which is made the retention member 16 or the defeatable portion 63, and that is the same of different as the material from which is made the housing 22, when present.

In some implementations, when the non-magnetic member 62 includes a defeatable portion 63, the non-magnetic member 62 can be made of an 85/15 (85% glycolic) PLGA or PDO, while the material used for forming the defeatable portion 63 can be made of a 90/10 (90% glycolic) or 95/5 PLGA. In this example, the 90/10 or 95/5 PLGA can have a faster dissolving rate and mechanical degradation rate compared to the 85/15 PLGA or PDO, which can enable the defeatable portion 63 to be defeated at a desired time point during or after the healing time period. Aside from the degradation differences due to hydrolysis, the materials may have different mechanical properties depending on ratios of glycolic:lactic which may inhibit or accelerate mechanical failure due do loading. The materials from which are made the components of the magnetic implant can thus be chosen to influence the extent of their respective degradation and/or mechanical failure (e.g., fracture due to loading), which in turn can impact the moment when given components are going to detach or separate from each other to facilitate their excretion. Furthermore, providing the non-magnetic member 62 made of a defeatable material, whether a defeatable portion 63 is present or not, can enable the non-magnetic member 62 to have its size reduced over time, which can also facilitate its excretion.

Housing

In implementations where the magnetic member 60 includes a housing 22, various scenarios are possible with regard to the respective materials from which the magnetic member 60 and the non-magnetic member 62 can be made. The housing 22 and the non-magnetic member 62 can be made of similar or same materials. Alternatively, the housing 22, or a portion thereof, and the non-magnetic member 62 can be made of different materials.

For instance, in the implementation shown in FIGS. 15-20, the non-magnetic member 62 and the portion housing the magnet, i.e., the housing 22, can be made of a defeatable material as described above, with the defeatable portion 63 being made of the same material or of a material that has a faster dissolving rate and mechanical degradation rate compared to the housing 22 and the non-magnetic member 62. These considerations are also applicable to the implementation shown in FIGS. 1-14, with a housing 22 that can be made of a defeatable material, or of a material that is generally not susceptible to dissolution or degradation, and that would be considered a durable material once implanted in the hollow organ.

The materials can also be chosen taking into consideration the configuration of the housing 22. For instance, when the housing includes two halves such as shown in FIGS. 2 and 15, the housing 22 can be made of a metal or a polymer. When made of a metal, the two halves of the housing 22 can be joined together by welding, or using an adhesive, for instance. An example of a metal that can be used to house the magnet 24 is titanium. When the housing 22 comprises titanium, the titanium can serve as a mechanical skin provided over the magnet 24. When made of a polymer, the two halves of the housing 22 can be joined by bonding, or using an adhesive, for instance. The degree of rigidity of the plastic can range from soft to stiff depending on the design of the housing 22. Examples of suitable polymers that can be used for forming the housing 22 can be polyether ether ketone (PEEK), which is a medical grade material that can be considered as a stiff polymer, and thermosetting resins, including photopolymers that undergo selective photopolymerization, or curing, in a vat when exposed to a UV light source, such as in 3D resin printing.

In some implementations, the magnetic implant can include a retention member and/or a defeatable portion, a non-magnetic member and a magnetic member that includes a housing, with the retention member and/or the defeatable portion, the non-magnetic member and the housing being made of different materials. For instance, the retention member or the defeatable portion can be made of a material A, that is bioerodible, biodegradable, and/or bioresorbable, or that has a faster degrading rate compared to the materials of the other components of the magnetic implant. The non-magnetic member and the housing can be made of another material B, C, or D, etc., depending on the desired time-based mechanical properties. For example, the housing can be printed layer by layer to encapsulate the magnet out of rigid material such as peek, polycarbonate, or another material, while the retention member or defeatable portion can be made of a bioerodible, biodegradable, and/or bioresorbable material such as PLGA, PDO, or another material, and the non-magnetic member can be made of a third material that is either rigid or bioerodible, biodegradable, and/or bioresorbable.

Additional Considerations Regarding the Housing, the Non-Magnetic Member and the Retention Member In some implementations, an additive manufacturing method can be used to manufacture the housing 22, the non-magnetic member 62 and/or the retention member 16. An additive manufacturing method can refer to a method for manufacturing a three-dimensional object by adding layer over layer of given material(s) to obtain a plurality of layers according to a three-dimensional model, the plurality of successive layers being bonded together, for instance by sintering or melting, to form the three-dimensional object. In some implementations, the additive manufacturing method is a 3D printing method. The additive manufacturing method can facilitate the production of objects having complex geometries, compared to conventional subtractive methods.

Additive manufacturing methods encompass a broad spectrum of methods, such as, but not limited to, binder jetting, directed energy deposition, material extrusion such as fused deposition modeling (FDM), material jetting, powder bed fusion, sheet lamination, vat photopolymerization, combinations thereof, or any other method(s) as known in the art.

In some implementations, the housing 22 may be formed of one or multiple pieces. For instance, FIGS. 2 and 15 show a magnetic implant that includes a housing having a top and bottom with a parting line where they mate together once assembled, also referred to as the outward portion 26 and the inward portion 28. The parting line may be incorporated anywhere along the thickness of the magnetic implant. The clamshell construction allows for easy assembly and encapsulation of the component parts that reside within the housing 22, such as the magnet 24, the delivery system attachment mechanisms, etc. The housing 22 and its internal components may be bonded together using adhesives, thermally reflowed or overmolded if the housing 22 is formed of a thermoplastic resin. If the housing 22 is made of a metallic material, the parting line of the outward portion 26 and the inward portion 28 may be laser welded to bond the outward portion 26 and the inward portion 28 together and create a hermetic seal around the magnetic core, or magnet 24. Alternatively, portions of the housing 22 can be coupled via a snap-on mechanism, for instance. FIG. 14 illustrates an implementation where the housing 22 is made of a single piece.

Delivery of the Pair of Magnets

Figure 5:
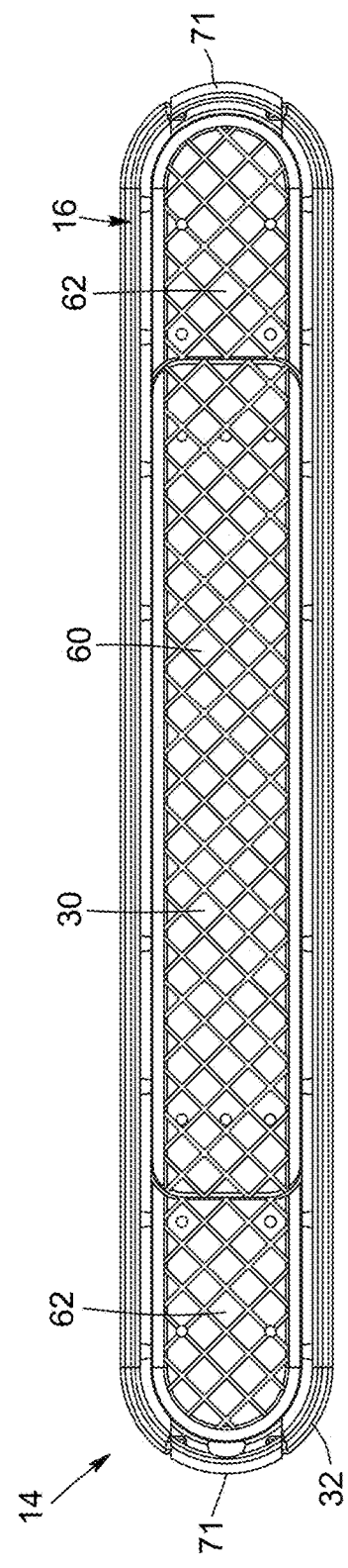
FIG. 5 is a top view of the second magnetic implant of FIG. 1.
Figure 7:
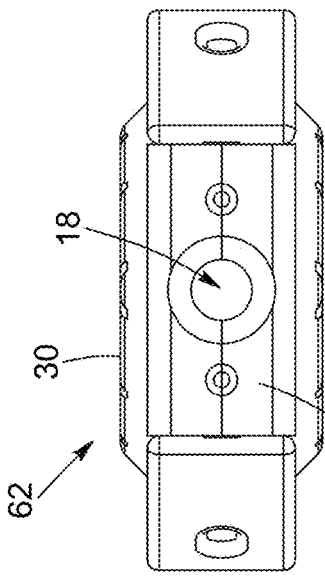
FIG. 7 is a side view of the second magnetic implant of FIG. 1, showing the second longitudinal end thereof.
Figure 6:
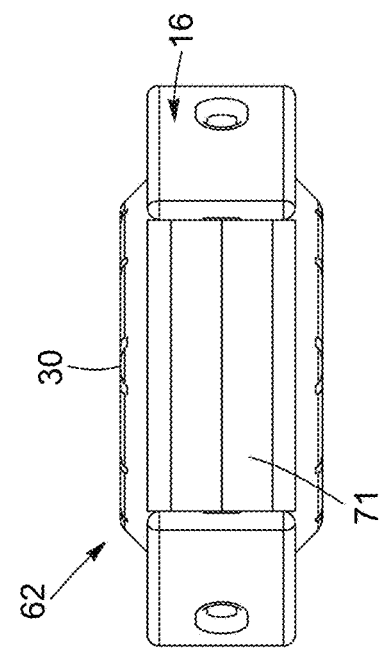
FIG. 6 is a side view of the second magnetic implant of FIG. 1, showing the first longitudinal end thereof.
Figure 8:
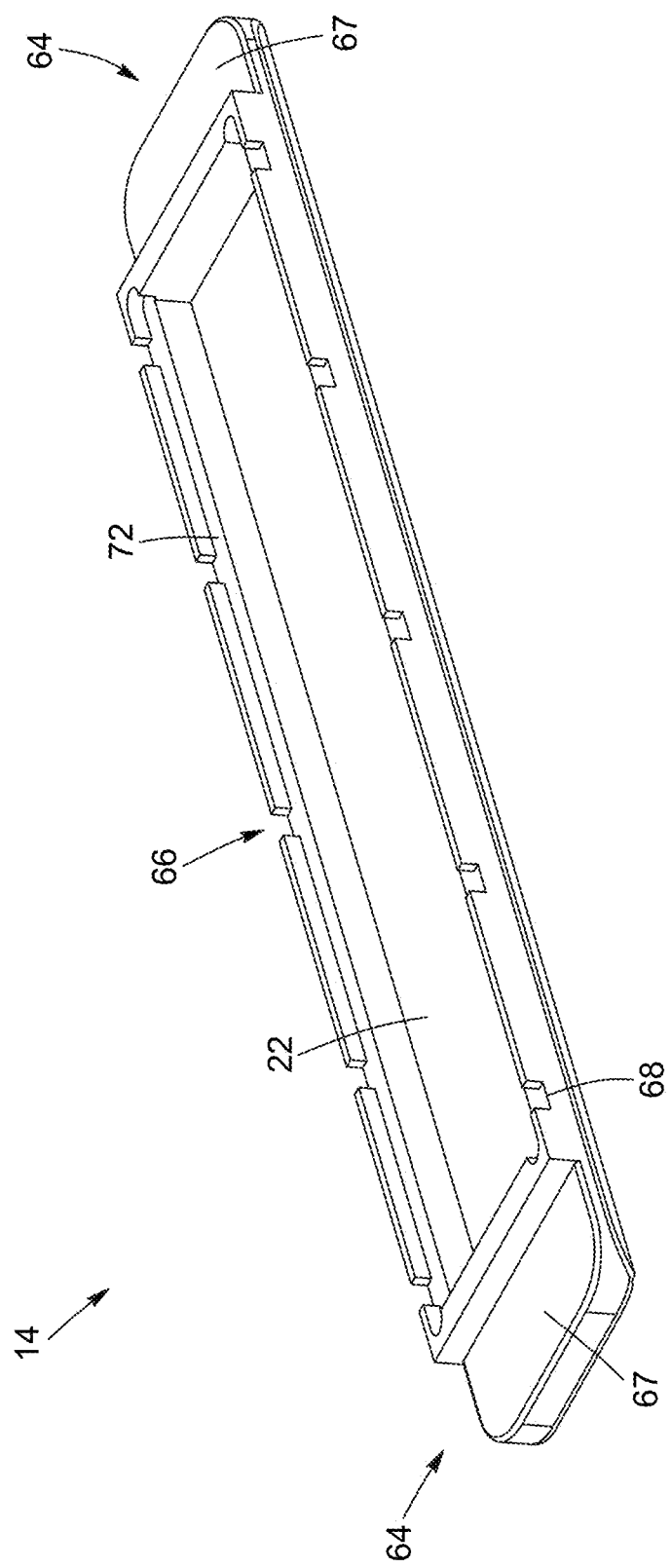
FIG. 8 is a perspective view of the half of the housing shown in FIG. 3.

Each one of the first and second magnetic implants 12, 14 can include a connecting member 18 connectable to a corresponding connector extending from a corresponding endoscope to be releasably engageable with the connector. The corresponding connector can be for instance a delivery catheter 20. With reference to FIG. 5, when the connector is a delivery catheter, the connecting member 18 can include a delivery catheter attachment assembly 46 connectable to the delivery catheter 20.

The implementations shown in FIGS. 1-20 are provided as examples among various configurations that the connecting member and the connector can take. Accordingly, it is to be understood that the drawings and descriptions herein are proffered by way of example only, and that other types of connector and connecting member can also be suitable to enable the connection of the magnetic implant with a delivery device, such as an endoscope, so that the magnetic implant can be delivered to the site of the desired anastomosis. For instance, as mentioned above, the connecting member can include a loop, such as a loop made of a wire, that extends outwardly from a corresponding magnetic implant to enable grasping by a distal end of a connector, such as a delivery catheter.

Methods for Forming an Anastomosis in the Digestive Tract

A method for forming an anastomosis between two adjacent walls of a digestive tract of a patient will now be described in further detail. The method can include navigating a first magnetic implant into the digestive tract of a patient to a first location, on one side of a desired anastomose site, within the lumen of a first hollow organ, and navigating a second magnetic implant into the digestive tract of the patient to a second location on another side of the desired anastomose site, within the lumen of a second hollow organ.

Various techniques can be used to navigate, or deliver, the first and second magnetic implants. It is to be noted that a chosen technique for navigating or delivering the first magnetic implant can be the same or different from the chosen technique for navigating or delivering the second magnetic implant. In some implementation, the navigation of the magnetic implant can be performed via a natural cavity of the patient, i.e., the mouth or the anus, using for example an endoscopic device.

In some implementations, navigating the first and second magnetic implants can include releasably engaging the first and second magnetic implants with a corresponding delivery catheter insertable in a working channel of a corresponding endoscope via a connecting member.

In some implementations, at least one of the first and second magnetic implants can be navigated to the site of the desired anastomosis using a laparoscopic procedure. Details regarding various types of suitable laparoscopic procedures and laparoscopic instruments and devices can be found described in U.S. Patent Application No. 2020/0138438A1 and U.S. application Ser. No. 17/524,502, which are incorporated herein by reference in their entirety.

Once the magnetic implants are delivered within their respective hollow organ and on their respective side the of the desired anastomosis, the first and second magnetic implants can be brought in close proximity to enable magnetic coupling of the first and second magnetic implants through the two adjacent vessel walls of the digestive tract, such that the compression surface of each of the first and second magnetic implants contacts the interior wall of their respective hollow organ at the site of the desired anastomosis. The magnetic coupling of the two magnetic implants compresses a portion of the two adjacent walls therebetween, and the portion of the adjacent walls that is compressed between the respective compression surfaces of the magnetic implants eventually forms a necrotic area as the blood flood supply to this area progressively declines.

As at least one of the first and second magnetic implants includes a retention member extending outwardly therefrom, i.e., outwardly from a peripheral wall of the corresponding magnetic implant, the first and second magnetic implants are retained in position on either side of the two adjacent walls during a healing time period to enable formation of a scarred edge surrounding the necrotic area. Retaining the first and second magnetic implants in position during the healing time period prevents the coupled first and second magnetic implants to pass through the necrotic area prematurely, e.g., before the healing time period is completed. Furthermore, the retention member enables the magnetic member and the non-magnetic member(s) of the magnetic implant to remain engaged together during the healing time period.

The retention member is configured so as to be defeatable once the healing time period is completed, by a combination of mechanisms that can include at least one of dissolution, degradation and fragmentation, to enable disengagement of the magnetic members from the non-magnetic members.

In some implementations, the first and second magnetic implants can be manipulated by using a magnet externally, for instance to facilitate the passing of the coupled magnetic implants via the bowel lumen of the patient. An endoscope can also be used to manipulate the coupled magnetic implants internally, also to facilitate their passing via the bowel lumen of the patient.

Several alternative implementations and examples have been described and illustrated herein. The implementations of the technology described above are intended to be exemplary only. A person of ordinary skill in the art would appreciate the features of the individual implementations, and the possible combinations and variations of the components. A person of ordinary skill in the art would further appreciate that any of the implementations could be provided in any combination with the other implementations disclosed herein. It is understood that the technology may be embodied in other specific forms without departing from the central characteristics thereof. The present implementations and examples, therefore, are to be considered in all respects as illustrative and not restrictive, and the technology is not to be limited to the details given herein. Accordingly, while the specific implementations have been illustrated and described, numerous modifications come to mind.

The invention claimed is:

1. A system for forming an anastomosis between two adjacent walls of a digestive tract, the system comprising:
   first and second magnetic implants configured to magnetically couple to each other through the two adjacent walls of the digestive tract to compress a portion of the two adjacent walls therebetween and form a necrotic area that becomes surrounded by a scarred edge following a healing time period, at least one of the first and second magnetic implants comprising:
      a magnetic member comprising a magnet;
      a non-magnetic member provided in a longitudinally adjacent relationship relative to the magnetic member;
      the magnetic member and the non-magnetic together defining a substantially flat compression surface configured to contact wall tissue of the portion of the two adjacent walls; and a defeatable portion located between the magnetic member and the non-magnetic member, the defeatable portion being configured to temporarily retain the magnetic member and the non-magnetic member engaged together during the healing time period.

2. The system of claim 1, wherein the defeatable portion is thinner than a thickness of the magnetic member or narrower than a width of the magnetic member.

3. The system of claim 1, wherein the defeatable portion includes a plurality of struts.

4. The system of claim 1, wherein the defeatable portion includes a plurality of regions having a reduced thickness compared to a thickness of the magnetic member.

5. The system of claim 1, wherein the defeatable portion comprises at least one of a bioerodible material, a biodegradable material, and a bioresorbable material.

6. The system of claim 1, wherein the defeatable portion comprises at least two materials, the at least two materials having a different dissolution rate or a different degradation rate once implanted in a given environment.

7. The system of claim 1, wherein the defeatable portion comprises at least one notch or spot having a dissolution rate or a degradation rate that is different from a remainder thereof once implanted in a given environment.

8. The system of claim 1, wherein the magnetic member further comprises a housing configured to house the magnet therein.

9. The system of claim 1, wherein the non-magnetic member includes two halves.

10. The system of claim 1, wherein the non-magnetic member is made of a single component.

11. The system of claim 1, wherein the non-magnetic member comprises first and second non-magnetic members, the first non-magnetic member being provided at a first longitudinal end of the magnetic member and the second non-magnetic member being provided at a second longitudinal end of the magnetic member, and the defeatable portion comprising a first defeatable portion between the first non-magnetic member and the magnetic member and a second defeatable portion between the second non-magnetic member and the magnetic member.

12. The system of claim 1, wherein the defeatable portions of the first and second magnetic implants are made of a same material.

13. The system of claim 1, wherein the defeatable portion of the first magnetic implant is made from a different material than the defeatable portion of the second magnetic implant.

14. The system of claim 13, wherein the first magnetic implant is configured for implantation in a strongly acidic environment and the second magnetic implant is configured for implantation in a weakly acidic environment, and once implanted in the strong acidic environment and in the weak acidic environment respectively, the defeatable portion of the first and second magnetic implants have a similar dissolution rate or degradation rate.

15. The system of claim 1, wherein the defeatable portion is defeatable via a dissolution mechanism or a degradation mechanism.

16. A system for forming an anastomosis between two adjacent walls of a digestive tract, the system comprising:
   first and second magnetic implants configured to magnetically couple to each other through the two adjacent walls of the digestive tract to compress a portion of the two adjacent walls therebetween and form a necrotic area that becomes surrounded by a scarred edge following a healing time period, at least one of the first and second magnetic implants comprising:
      a magnetic member comprising a magnet, the magnetic member having an outer periphery;
      a non-magnetic member provided along at least a portion of the outer periphery of the magnetic member;
      the magnetic member and the non-magnetic together defining a substantially flat compression surface configured to contact wall tissue of the portion of the two adjacent walls; and
      a defeatable portion configured to temporarily retain the magnetic member and the non-magnetic member engaged together during the healing time period.

17. The system of claim 16, wherein the defeatable portion is provided between the magnetic member and the non-magnetic member.

18. The system of claim 16, wherein the non-magnetic member comprises first and second non-magnetic members, a first one of the non-magnetic members being provided on one lateral side of the magnetic member and a second one of the non-magnetic members being provided on another lateral side of the magnetic member, the first and second non-magnetic members being retained together via the defeatable portion.

19. The system of claim 16, wherein the non-magnetic member comprises first and second non-magnetic members, a first one of the non-magnetic members being provided on one longitudinal side of the magnetic member and a second one of the non-magnetic members being provided on another longitudinal side of the magnetic member, the first and second non-magnetic members being retained together via the defeatable portion.

20. The system of claim 16, wherein the magnetic member and the non-magnetic member of the at least one of the first and second magnetic implants comprises a lumen-oriented portion and a tissue-contacting portion, and the defeatable portion is provided on the lumen-oriented portion of the at least one of the first and second magnetic implants and spans transition from the magnetic member to the non-magnetic member.

21. The system of claim 16, wherein the defeatable portion comprises at least one of a bioerodible material, a biodegradable material, and a bioresorbable material.

* * * * *